United States Patent
Liu et al.

(10) Patent No.: US 6,316,002 B1
(45) Date of Patent: Nov. 13, 2001

(54) **GERMINATION ACTIVATED RED *GANODERMA LUCIDUM* SPORES AND METHOD FOR PRODUCING THE SAME**

(76) Inventors: Xin Liu, Building No. 391, 135 Xingang Xi Road, Guangzhou (CN); Chee-Keung Chung, Room 1505, Argyle Centre, 688 Nathan Rd., Mongkok, Kowloon (KR)

( * ) Notice: Subject to any disclaimer, the term of this patent is extended or adjusted under 35 U.S.C. 154(b) by 0 days.

(21) Appl. No.: 09/524,508

(22) Filed: Mar. 13, 2000

Related U.S. Application Data

(60) Provisional application No. 60/158,377, filed on Oct. 12, 1999.

(51) Int. Cl.$^7$ ............................ A61K 35/00; A61K 35/78
(52) U.S. Cl. ........................................ 424/195.15; 424/780
(58) Field of Search ............................... 424/195.15, 780

(56) References Cited

U.S. PATENT DOCUMENTS

| | | | |
|---|---|---|---|
| 4,472,907 | 9/1984 | Wada et al. | 47/1.1 |
| 5,595,742 | * 1/1997 | Fujiwara et al. | . |

FOREIGN PATENT DOCUMENTS

| | | | |
|---|---|---|---|
| 1101860 | * | 4/1995 | (CN) . |
| 1111529 | * | 11/1995 | (CN) . |
| 1118005 | * | 3/1996 | (CN) . |
| 1122658 | * | 5/1996 | (CN) . |
| 1134306A | * | 10/1996 | (CN) . |
| 1165032A | * | 11/1997 | (CN) . |
| 1245718 | * | 8/1998 | (CN) . |
| 1200286 | * | 12/1998 | (CN) . |
| 1205231 | * | 1/1999 | (CN) . |
| 1231925 | * | 10/1999 | (CN) . |
| 2240026 | | 9/1990 | (JP) . |
| 52041208 | | 8/1993 | (JP) . |

OTHER PUBLICATIONS

Jiang et al. Shipin Kexue (Beijing). vol. 17, No. 4, pp. 19–22, CAPLUS Abstract enclosed, 1996.*

Yang et al. Zhongcaoyao. vol. 28, No. 12, pp. 721–723, CAPLUS Abstract enclosed, 1997.*

Lee, Seung Y.; Cardiovascular Effects of Mycelium Extract of *Ganoderma lucidum*: Inhibition of Sympathetic Outflow as a Mechanism of Its Hypotensive Action, Chem Pharm. Bull. vol. 38, p. 1359–1364 (1990).

Kim et al., Int. J. Mol. Med vol. 4(3), p. 273–277 (1999).

Lin et al., J. Ethnopharmacol., vol. 47 (1), p. 33–41 (1995).

Mekkawy, SaHar et al., Anti–HIV–1 and Anti–HIV–A–Protease Substances from *Ganoderma Lucidum*; *Phytochemistry*, vol. 49(6), p. 1651–1657 (1998).

Wasser, Solomon P., et al., Therapeutic Effects of Substances Occurring in Higher Basidiomycetes Mushrooms: A Modern Perspective; *Crit. Rev. Immunol.*, vol. 19(1), p. 65–96 (1999).

Miyazaki, Toshio et al., Studies on Fungal PolysaccaridesXXVII. Structual Examination of a Water–soluble, Antitumor Polysaccaride of *Ganoderma lucidum; Chem. Pharm. Bull.*, vol. 29(12), p. 3611–3616 (1981).

Min, Byung–Sun et al.; Triterpenes from the Spores of *Ganoderma lucidum* and Their Inhibitory Activity against HIV–1 Protease; *Chem. Phar. Bull.*, vol. 46(10), p. 1607–1612 (1998).

Kino, K. et al., An immunomodulating protein, Ling Zhi–8(LZ–8) prevents insulitis an non–obese diabetic mice; *Diabetolgia*, vol. 33, p. 713–718 (1990).

Lieuwe, G. et al.; Ling Zhi–8: Studies of a New Immunomodulating Agent; *Transplantation*, vol. 60, p. 438–443 (1995).

Kino, Kohsuke et al.; Immunomodulator, LZ–8, Prevents Antibody Production in Mice; *Int. J. Immunopharmac.*, vol. 13(8), p. 1109–1115 (1991).

Maruyama, Hirofumi; Antitumor Activity of *Sarcodon aspratus* (BERK>)S. Ito and *Ganoderma lucidum* (FR.) Karst.; *J. Pharmacobio–Dyn.*, vol. 12, p. 118–123 (1989).

Shimizu, Akria et al.; Isolation of an Inhibitor of Platelet Aggregation from a Fungus, *Ganoderma lucidum; Chem. Pharm. Bull.*, vol. 33, p. 3012–3015 (1985).

Morigiwa, Aiko et al.; Angiotension Converting Enzyme–Inhibitory Triterpenes from *Ganoderma lucidum; Chem. Pharm. Bull.*, vol. 34(7), p. 3025–3028 (1986).

Kanmatsuse, Katsuo et al.; Studies of *Ganoderma lucidum*. I. Efficacy against Hypertension and Side Effects; *Yakugaku Zasshi*, vol. 105(10), p. 942–947 (1985).

Lieu, Chien–Whei et al.; The Effect of *Ganoderma lucidum* on Induction of Differentiation in Leukemic U937 Cells; *Anticancer Research*, vol. 12, p. 1211–1216 (1992).

(List continued on next page.)

*Primary Examiner*—Christopher R. Tate
(74) *Attorney, Agent, or Firm*—Fei-Fei Chao; Venable, Baetjer, Howard & Civiletti, LLP

(57) ABSTRACT

The present invention describes a method for germination activating spores of red Ganoderma lucidum to produce bioactive substances which has medicinal effects on patients with immunological disorders, cancer, AIDS, hepatitis, diabetes, and cardiovascular diseases, and can prevent or inhibit free radical oxidation and hepatotoxic effects. The method can be subdivided into three stages. At the first stage, a germination activation method is introduced which includes soaking the spores in a solution to induce germination, and placing the germination treated spores in a culture box to induce the synthesis of bioactive substances and softening of the cell walls of the spores. At the second stage, sporoderm-broken ganoderma spores are collected by treating the epispores with cell wall breaking enzymes and/or mechanical force. At the last stage, the bioactive substances are extracted from the sporoderm-broken spores by drying at low temperature followed by extraction.

22 Claims, No Drawings

OTHER PUBLICATIONS

Wang, Sheng–Yuan et al.; The Ani–Tumor Effect of Released from Activated Macrophages and T Lymphocytes; *Int. J. Cancer*, vol. 70, p. 699–705 (1997).

O'Neil, Carol E. et al.; Basidiospore Extracts: Evidence for Common Antigentic/Allergenic Determinants; *Int. Archs Allergy appl. Immun.*, vol. 85, p. 161–166 (1988).

Nogami, Mari et al.; Studies of *Ganoderma lucidum*VI. Anti–allergic Effect. (1); *Yakugaku Zasshi*, vol. 106(7), p. 594–599 (1986).

Liu, Gengtao et al.; Some Pharamacological Actions of the Spores of *Ganoderma Lucidum* and the Mycelium of Ganoderma Capense (Lloyd)Teng Cultivated by Submerged Fermentation; *Chinese Medical Journal*, vol. 92(7), p. 496–500 (1979).

Fu, Huidi et al.; The Clinical Effects of *Ganoderma Lucidum* Spores Preparations in 10 Cases of Atrophic Myotonia; *Journal of traditional Chinese Medicine*, vol. 2(!), p. 63–65 (1982).

Mizushina, Yoshiyuki et al.; A Mushroom Fruiting Body–Inducing Substance Inhibits Activities of Replicative DNA Polymerases; *Biochemical and Biophysical Research Communications*, vol. 249, p. 17–22 (1998).

Lin, Lee–Juian et al.; Separation of oxygenated triterpenoids from *Ganoderma lucidum* by high–performance liquid chromatography; *Journal of Chromatography*, vol. 410, p. 195–200 (1987).

Kino, Kohsuke et al.; Isolation and Characterization of a New Immunomodulatory Protein, Ling Zhi–8 (LZ–8), from *Ganoderma lucidium*; *The Journal of Biological Chemistry*, vol. 264, p. 472–478 (1989).

\* cited by examiner

GERMINATION ACTIVATED RED *GANODERMA LUCIDUM* SPORES AND METHOD FOR PRODUCING THE SAME

RELATED INVENTION

The present invention claims the priority of U.S. Provisional Application Serial No. 60/158,377, filed on Oct. 12, 1999, which is herein incorporated by reference.

FIELD OF THE INVENTION

The present invention relates to bioactive substances which are extracted from germination activated spores of *Ganoderma lucidum* Leyss ex Fr. Karst. It further relates to methods for culturing and producing such substances. Finally, it relates to the use and methods of using the bioactive substances produced by germination activated ganodenna spores for treating patients or mammals with immunological disorders, cancer, AIDS, hepatitis, diabetes, and cardiovascular diseases. The bioactive substances can also be used to prevent or inhibit free radical oxidation and hepatotoxic effect.

BACKGROUND OF THE INVENTION

Qanoderma (*Ganoderma lucidum* Leyss ex Fr. Karst) is a polyporous fungus. It belongs to the class Basidiomycetes, the family Polypolaceae, and the genus Ganoderma. Since ancient timnes, ganoderma has been praised as a miracle fungus for its capability of prolonging human life. It is believed that the medicinal effects of ganodenna lie upon the natural or bioactive substances it produces which can stimulate or modulate the neuro-endocrino-immuno system of human body to fight off diseases. Ganoderma is also well known for its antitumor and immune enhancing properties, (Kim et al., *Int. J. Mol. Med.* (1999), 4(3):273– 277), cardiovascular effects (Lee et al., *Chem. Pharm. Bull.* (1990), 38:1359–1364), as well as free radical scavenging and antihepatotoxic activities (Lin et al., *J. Ethnopharmacol.*, (I995), 47(1):33–41). Two substances extracted from ganodenna have been reported to especially relate to the medicinal effects of ganoderma. They are triterpene and polysaccharide, although so far no clinical evidence has been provided which supports the claims of medicinal effects of these substances. (Mekkawy et al., *Phaochemistry*, (1998), 49(6):1651–1657; Wasser et al., *Crit. Rev. Immunol.*, (1999), 19(1):65–96).

Ganoderma is the most rare and valuable herb in Chinese medicine. It is known in China for over 5,000 years as "ling zhi". There are a variety of ganodenma, for instance, *G. lucidum* (red), *G. applanatum* (brown), *G. tsugae* (red), *G. sinense* (black), and *G. oregonense* (dark brown). However, due to the fact that wild types of ganoderma only grow naturally and very rarely on aged trees in steep mountains, research which requires a constant supply of high quantity and quality of ganoderma has rarely been conducted.

Not until recently, after the development of artificial cultivation techniques, methods for artificially cultivating *Ganodenna lucidum* (Fr) Karst have been developed. (see e.g., U.S. Pat. No. 4,472,907). The newly developed cultivation methods allow researchers to produce sufficient amount of ganoderma for the studies.

Although it is believed that the spores of ganoderma represent the essence of ganoderma because they contain all the bioactive substances of ganoderma, most of the ganoderma studies are conducted using the fruit body or mycelium of ganoderma as experimental materials. Ganoderma spores are rarely studied.

Ganoderma spores are tiny and mist-like spores of 5~8 $\mu$m in sizes which have extremely hard and resilient, double-layer epispores, thus making them difficult to break open. The ganoderma spores normally scatter at the pelius of mature ganoderma. When mature, the ganoderma spores are ejected from the pileus. Such ejected ganodenna spores are collectively called "spore powders". In the wild, the "spore powders" are difficult to collect because of the following reasons: (1) the germination rate (i.e., about 3–15%) of the spores is extremely low; (2) the ejection period is relatively short (i.e., approximately 10 days per lifecycle); and (3) some environmental factors, such as wind and rain, may also hinder the collection of the spores. In addition, the substances of the collected spores are difficult to extract due to the resiliency of the epispores.

In recent years, there have been reports which disclose methods for breaking the cell walls of the *Ganoderma lucidum* spores. For example, JP52041208 discloses the extraction of effective components of spores of "shiitake" by efficient mechanical breaking of the cell membranes. JP2240026A discloses the use of solvent to break open the ganoderma spores. CN1134306 discloses a method for producing sporoderm-broken *Ganoderma lucidum* sporopollen which combines water soaking, air-drying and microwave heating treatment. CN1165032 discloses a method for breaking the skin of spore powder of *Ganoderma lucidum* with a skin-dissolving enzyme such as lysozyme, snail enzyme, cellulase and hemicellulase, followed by freezing and melting in enzymolized liquid, and ultrasound.

With the improvement of the spore breaking techniques, more research which directed to the studies of the ganoderma spores has been undertaken. However, the improvement of the spore breaking techniques does not overcome the shortcoming of the low germination rate of the spores. In fact, due to the low germination rate, most of the studies on ganoderma spores are conducted using the extraction of bioactive substances from spores representing an array of dormant to various germination stages. Because the spores at different stages of the lifecycle produce different kinds and/or proportions of bioactive substances, each batch of the mixture of the spores thus contains different active ingredients. The results from such studies are apparently meaningless since no proper controls can be provided.

In the invention to be present below, a germination activation method will be introduced. This method can successfully activate the dormant ganoderma spores and increase the germination rate of the ganoderma spores to more than 95%. The present invention also provides a unique spore breaking method which not only allows for the high recovery of the bioactive substances in the spores, but also successfully preserves the functional activities of the bioactive substances. Finally, the present invention provides clinical studies which demonstrate the significance of the bioactive substances extracted from the germination activated ganoderma spores in treating patients or mammals with immunological disorders, cancer, AIDS, hepatitis, diabetes, and cardiovascular diseases. The bioactive substances can also be used to prevent or inhibit free radical oxidation and hepatotoxic effect.

SUMMARY OF THE INVENTION

The present invention provides a method which can significantly increase the germination rate of the spores of red *Ganoderma lucidum*. When the dormant spores of red *Ganodenna lucidum* are activated by germination, they produce bioactive substances which contain, but are not limited to, active genes and promoters, active enzymes, sterols, cytokines, interferons, lactone A, ganoderma acid A, triterpenes, polysaccharides, vitamins, superoxide dismutases (SOD), vitamin E, glycoproteins, growth factors, etc. These bioactive substances, in their entirety, demonstrate superb medicinal effects.

This method requires soaking the ganoder4a spores in a solution to induce germination. The solution used for this purpose includes clear or distilled water, salie solution, and any nutritional solution. Examples of the nutritional solution include coconut juice, 1–5% malt extract solution, 0.5–25% extracts of the ganodermna sporocarps or capillitia, 0.1–5% of culture solution containing biotin, 0.1–3% of culture solution containing monobasic potassium phosphate and magnesium sulfate. One or more of the above listed nutritional solution can be used, with the amount added being 0.1–5 times of the weight of the ganoderma spores. The spores are soaked in the solution for 30 minutes to 8 hours at 20–43° C., preferably for 2 to 4 hours and between 25 and 35° C.

The germination induced ganoderma spores are placed in a well-ventilated culture box which is controlled with constant temperature and constant humidity to activate the synthesis of bioactive substances. The relative humility is at 65–98%, preferably 85–97%, and the temperature is at 18–48° C., preferably at 25–35° C.

The present invention also provides a method for producing sporoderm-broken ganoderma spores. The method requires treating the germination activated ganoderma spores with enzymes which can dissolve the cell walls of the spores or a mechanical force or both. Examples of the lytic enzymes include chitinase or cellulase. The types of mechanical force include micronization, roll pressing, grinding, ultrasound, and super high pressure microstream treatment. A combination of one or more kinds of mechanical force with enzymolysis is preferred.

The present invention further provides a method for extracting bioactive substances from the germination activated ganoderma spores. The method requires drying the sporoderm-broken ganodermna spores at low temperature, followed by extracting the dried sporoderm-broken ganoderma spores with a solvent. The drying method can be either a freeze-drying or a vacuum-drying. The bioactive substances can be extracted either by water or by organic solvents such as alcohol, ether, acetone etc. or by both. They can also be extracted by thin film condensation.

Either the sporoderm-broken ganoderma spores or the extracted bioactive substances can be formulated by any conventional drug delivery systems to be orally administered to patients or mammals.

In addition, the present invention provides methods for using the bioactive substances to treat patients with immunological disorders, cancer, AIDS, hepatitis, diabetes, cardiovascular diseases, and bacterial or viral infections. The invention also provides method to use the bioactive substances for preventing free radical oxidation and inhibiting hepatotoxic effects.

Finally, the present invention provides uses of the bioactive substances as agents for treating immunological disorders (such as dysfunction of the nervous system and neuromusculature including multiple sclerosis, myotonias and muscular dystrophy), cancer, AIDS, hepatitis, diabetes, cardiovascular diseases, and bacterial or viral infections. The bioactive substances can also be used as agents for antioxidant and anti-hepatotoxic effects.

DETAILED DESCRIPTION OF THE INVENTION

The tiny spore of *Ganoderma lucidum* has an extremely hard and resilient, double-layered epispore. In the wild, the germination of the spores of *Ganoderma lucidum* is relatively slow and their germination rate is extremely low. In fact, it takes about 24 to 48 hours for the germ tubes of the spores start to sprout under proper conditions, and the capillitia start to form branches after 72 hours, with a germination rate of only 3–15%.

Using the method of the present invention, mature spores of red *Ganoderma lucidum* were selected to undergo processing treatment. There are three distinctive stages for the spores processing treatment. The goal is to effectively preserve the large amount of bioactive substances produced by the germination activated spores. The first stage involves the induction of germination which can be achieved by soaking the spores in a solution for a period of time, followed by cultivating the germination induced spores in a well-ventillated culture box. The second stage involves the production of sporoderm-broken (i.e., by breaking up the cell walls of epispores) spores which can be achieved by enzyme treatment and/or mechanical force. The final stage involves the extraction of bioactive substances from the sporoderm-broken spores which can be achieved by freeze-drying or vacuum drying followed by extraction with solvent or by thin film condensation.

Below are general descriptions of the inventive steps which lead to the production of bioactive substances:

I. Soaking to induce germination: Mature and perfect spores of red *Ganoderma lucidum* were carefully selected to undergo a soaking process to induce germination. Spores were kept in clear or distilled water, biological saline solution, or other nutritional solutions that could enable the spores of red *Ganoderma lucidum* to germinate rapidly. Examples of nutritional solutions include coconut juice or a 1–5% malt extract solution, 0.5–25% extracts of *Ganoderma lucidum* sporocarps or *Ganoderma lucidum* capillitia, 0.1–5% of culture solution containing biotin, 0.1–3% of culture solution containing potassium phosphate (monobasic) and magnesium sulfate. The choice of solution would depend on the soaking time required, the amount of spores to be processed and other such factors as availability of materials. One or more of the above germination solutions could be used, with the amount added being 0.1–5 times the weight of the spores of red *Ganoderma lucidum*. The soaking time can be determined according to the temperature of the water, and usually the soaking was carried out for 30 min to 8 hours with the temperature of the water at 20–43° C. Preferably soaking times were 2–4 hours, and temperature of the water was 25–35° C.

II. Activation culture: The spores of red *Ganoderma lucidum* were removed from the soaking solution and excess solution was eliminated by allowing it to drip. The spores were then placed in a well-ventilated culturing box at a constant temperature and humidity so that spore activation culture could be carried out. The relative humidity of the culture was generally set at 65–98%, the culture temperature at 18–48° C. and the activation time lasted from 30 min to 24 hours. Preferably humidity is 85–97% and temperature is 25–35° C. Using the method provided by the present invention, the activation of spores of red *Ganoderma lucidum* reached a rate of more than 95%. During activation, the cell walls of the spores of red *Ganoderma lucidum* were clearly softened such that it was easier to penetrate the cell walls of the spores.

III. Treatment of the epispores: After the germination activation process, the spores were treated by enzymolysis. This process was carried out at a low temperature and under conditions such that enzyme activity was maintained, using chitinase, cellulase, or other enzymes, which are commonly used in the industry. The process was complete when the epispores lost their resilience and became brittle. Alternatively, physical treatments were carried out to penetrate the cell walls, for example, micronization, roll pressing, grinding, super high pressure microstream treatment, and other mechanical methods commonly used in the industry could be carried out, with a penetration rate of over 99%.

IV. Drying or extraction: Drying was carried out at low temperature using standard methods including freeze-drying or vacuum-drying etc., which are commonly used in the industry. The obtained product had a moisture content less than 4%. After drying, the bioactive substances were extracted by water or alcohol, or by thin film condensation. The extracted bioactive substances could be further purified by dialysis to ensure no contamination in the final products.

V. Pharmaceutical formulations of the bioactive substances: The bioactive substances can then made into purified powders, extract pastes, solutions for injection, or for oral consumption. The invention also encompasses the manufacture of pharmaceutical preparations of the active substances, using well known excipients and methods of manufacture known in the art. In addition, the bioactive substances can be dosed by any convenient method including, but not limited to, tablets, capsules, solutions, suppositories, nasal sprays, or injection devices. The choice of method for administration is determined by the clinical situation of the patient. The bioactive substances of the present invention, produced by the methods described, include active genes, inducers of the biotic potential promotor, inducers of the multicellular activator, inducers of interferon, lactone A, ganoderma polysaccharide, ganoderma spore fatty acids, ganoderma spore long chain alkyl hydrocarbons, ganoderma triterpenes, sterols, superoxide dismutase, vitamin E, active glycoprotein, certain growth factors, ganoderma acid A, superoxide dismutases (SOD), active glycoproteins, multiple active enzymes, and growth factors and so on. These bioactive substances, in a whole, contribute to the therapeutic uses described in the later sections.

The present invention will be further explained by way of illustrations. The illustrations can be divided into three different categories: (1) The "Manufacturing Examples", which describe various methods for producing the bioactive substances; (2) the "Experimental Examples", which describe various experimental testing using animals as models; and (3) the "Clinical Examples", which describe the treatment of the bioactive substances to patients with various diseases and the outcomes of such treatment. The "Clinical Examples" are especially appealing because they demonstrate that the bioactive substances have therapeutic effects on a variety of diseases. For example, patients with serious diseases, which include hepatitis B, cancer, and HIV or AIDS, have shown drastic improvement after the treatment of the bioactive substances extracted from the spores. Patients with diseases associated with immunological disorders such as dysfunction of the nervous system and neuromusculature (e.g., multiple sclerosis, myotonias and muscular dystrophy), have also shown improvement after taking the bioactive substances. In addition, the bioactive substances have applications in treatment of bacterial or viral infections, including tuberculosis and influenza. They also display positive effects in treating patients with insufficient hormone levels such as diabetes or thyroid insufficiencies. A further benefit of using the bioactive substances extracted from ganoderma spores is that they are non-toxic so that higher dosage can be prescribed to the patients.

MANUFACTURING EXAMPLES

Manufacturing Example 1

1. One hundred (100) kg of mature and perfect spores of red *Ganoderma lucidum* were carefully selected and 100 kg of 1% malt extract was added to the spores to carry out a soaking treatment to induce germination for 6 hours. The temperature of the water was set at 20° C.

2. After the soaking treatment, the spores were removed and the excess solution was eliminated by allowing them to drip. The spores were then placed in a well-ventilated culturing box with a constant temperature and humidity to undergo spore activation culture. The relative humidity of the culturing box was 70%, the culture temperature at 20° C., and the activation period lasted for 12 hours. After exarnination, it was found that the activation rate of the spores of red *Ganoderma lucidum* reached 96%, and the epispores were clearly softened during activation.

3. Micronization was used as the penetration method. After a micronization, the penetration rate of the epispores of red *Ganoderma lucidum* reached 99%.

4. Drying treatment was carried out in a standard vacuum drying apparatus, and the obtained product had a moisture content less than 3%.

5. The bioactive substances of the product obtained were measured using standard chemical analyses.

Manufacturing Example 2

1. One hundred (100) kg of mature and perfect spores of red *Ganoderma lucidum* were selected and 45 kg of coconut juice and 100 kg of distilled water were added to the spores to carry out a soaking treatment for 30 min. The temperature of the water was maintained at 35° C.

2. After the soaking treatment to induce germination, the excess solution was eliminated by allowing it to drip, and the spores were placed in a well ventilated culturing box at a constant temperature and humidity to carry out activation culture. The relative humidity of the culturing box was 80%, the temperature 36° C., and the activation period lasted for 5 hours. After examination with an electron microscope, it was found that the spores of red *Ganoderma lucidum* were in a state of activation, with the occurrence of a basic formation of the germ tube, and the epispores were clearly softened during the activation period.

3. Enzymolysis of spores was carried out for 3 hours, using 0.1 kg of chitinase, and 0.1 kg of cellulase with the enzymolysis temperature set at 40–55° C. After 2 hours, the hard and resilient double-layered cell walls of the spores were no longer resilient and became brittle. In another method, a further treatment was carried out using a micronizer to penetrate the cell walls and the penetration rate of the spores of red *Ganoderma lucidum* reached 99%.

4. A drying treatment was carried out using a standard freeze-drying apparatus, and the product obtained had a moisture content less than 2.8%.

5. The bioactive substances of the product obtained were measured using the standard chemical analyses.

Manufacturing Example 3

1. One hundred (100) kg of mature and perfect spores of red *Ganoderma lucidum* were carefully selected and 150 kg of 5% extract of the *Ganoderma lucidum* sporocarps as nutritional solution were added to the spores to carry out a soaking treatment for 4 hours, with the temperature of the solution set at 30° C.

2. After the soaking treatment to induce germination, the excess solution was eliminated by allowing it to drip and the spores were placed in a well-ventilated culturing box at a constant temperature and constant humidity to carry out activation culture. The relative humidity of the culturing box was 65%, the temperature at 38° C., and the activation period lasted for 5 hours. When examined under the electron microscope, it was found that the spores were in a state of activation, but no formation of the germ tube occurred yet and the epispores were clearly softened during the activation period.

3. After a treatment using a super high pressure microstream apparatus was carried out to penetrate the cell walls, the penetration rate of the spores of red *Ganoderma lucidum* was over 99%.

4. A drying treatment was carried out using a standard freeze-drying method, and the product obtained had a moisture content of less than 3.2%.

5. The bioactive substances of the product obtained were measured using the standard chemical analyses.

Manufacturing Example 4

1. One hundred (100) kg of mature and perfect spores of red *Ganoderma lucidum* were carefully selected and 200 kg of a culture solution containing 2% biotin were added to the spores. The soaking treatment to induce germination lasted for 3 hours, with the temperature of the solution set at 40° C.

2. After soaking, the spores were removed and the excess water was eliminated by allowing it to drip. The spores were then placed in a well-ventilated culturing box at a constant temperature and humidity to carry out activation culture. The relative humidity of the culturing box was 90%, the temperature at 33° C., and the activation period lasted for 4 hours. It was found that the activation rate of the spores reached 95%, and the epispores were clearly softened during the activation period.

3. Enzymolysis with 0.08 kg chitinase, and 0.2 kg cellulase of the spores was carried out for 3 hours at 40–55° C. At the end of the process, the hard and resilient double-layered cell walls of the spores were no longer resilient and became brittle. Then, a roll pressing treatment was carried out using a press roller. The penetration rate of the spores was over 99%.

4. A drying treatment was carried out for 12 hours in a standard, low temperature, blow drying apparatus and the product obtained had a moisture content less than 4%.

5. The bioactive substances of the product obtained were measured using the standard chemical analyses.

Manufacturing Example 5

1. One hundred (100) kg of mature spores of red *Ganoderma lucidum* were carefully selected and 100 kg of a culture solution of 0.1% potassium phosphate (monobasic) and magnesium sulfate was added to the spores to carry out a soaking treatment to induce germination for 8 hours, with the temperature of the solution set at 21° C.

2. After the soaking, the excess solution was eliminated by allowing it to drip, and the spores were placed in a well-ventilated culturing box at a constant temperature and humidity to carry out activation culture. The relative humidity of the culturing box was 85%, the temperature at 42° C., and the activation period lasted for 3 hours. When examined under the electron microscope, it was found that the spores of red *Ganoderma lucidum* were in a state of activation, the formation of buds had occurred and the epispores were clearly softened during the activation period.

3. Extraction was carried out with water, followed by a second extraction with alcohol. The extract solutions were combined and concentrated using a thin film technique.

4. Further processing was carried out to make purified powders, extract pastes, solutions for injection or oral consumption.

5. The bioactive substances of the product obtained were measured using the standard chemical analyses.

Manufacturing Example 6

1. One hundred (100) kg of mature and perfect spores of red *Ganoderma lucidum* were carefully selected. 50 kg of an extract solution of *Ganoderma lucida* containing 5% capillitia and 50 kg of a 1% malt extract were added to the spores and soaked for 7 hours to induce germination, with the temperature of the solution set at 25° C.

2. After the soaking treatment to induce germination, the excess solution was eliminated by allowing it to drip and the spores were placed in a well ventilated culturing box at a constant temperature and constant humidity to carry out activation culture. The relative humidity of the culturing box was 85%, the temperature at 25° C., and the activation period lasted for 12 hours. When examined under the electron microscope, it was found that the spores of red *Ganoderma lucida* were in a state of activation, however, formation of the germ tube had yet to occur and the epispores were clearly softened during the activation period.

3. After treatment with a super high pressure microstream apparatus to penetrate the cell walls was carried out, the penetration rate of the spores of red *Ganoderma lucidum* was over 99%.

4. A drying treatment was carried out using a standard freeze-drying method, and the product obtained had a moisture content less than 2.8%.

5. The bioactive substances of the product obtained were measured using the standard chemical analyses.

Manufacturing Example 7

1. One hundred (100) kg of mature and perfect spores of red *Ganoderma lucidum* were carefully selected and 300 kg of distilled water at 32° C. were added to the spores to carry out a soaking treatment for 8 hours.

2. After the soaking treatment to induce germination, the excess water was eliminated by allowing it to drip and the spores were placed in a well-ventilated culturing box at a constant temperature and humidity to carry out activation culture. The relative humidity of the culturing box was 95%, the culture temperature at 35° C., and the activation period lasted for 24 hours. When examined under the electron microscope, it was found that the spores of red *Ganoderma lucidum* were in a state of activation, however, no formation of the germ tube occurred yet and the epispores were clearly softened during the activation period.

3. After micronization, the penetration rate of the spores of red *Ganoderma lucidum* reached 99%.

4. A drying treatment was carried out using a standard vacuum drying apparatus, and the product obtained had a moisture content less than 3.5%.

5. The bioactive substances of the product obtained were measured using the standard chemical analyses.

EXPERIMENTAL EXAMPLES

The bioactive substances used in the following experiments were extracted from ganoderma spores which have been processed by germination activating, sporoderm breeding with enzyme engineering and freeze drying technology. The bioactive materials include, but are not limited to, ganoderma polysaccharides, ganoderma spore fatty acids, ganoderma spore long chain alkyl hydrocarbons, ganoderma triterpenes, superoxide dismutase, vitamin E, active glycoproteins, some growth factors, etc. It has been demonstrated that the completely wall-broken ganoderma spores show much more efficient physiological activities than ordinary ganoderma spores.

Experimental Examples 1

Free Radical Scavenging Effect of Sporoderm-Broken Ganoderma Spores by Testing on the Levels of malondialdehyde (MDA) in Tumor Tissues 1. Materials and Methods 1.1 Materials NIH mice used in the tests were supplied by the Test Animals Center of the Department of Health, Guangdong Province. The mice weighed 20–22 g, half of them being male, half female. The mouse reticulosarcoma (L-II) was supplied by the present Institute. A 0.2 g/mL oral solution using *Ganoderma lucidum* spore powder was prepared. Adriamycin (ADM) was manufactured by the Wan Le Pharmaceutical Co. Ltd. in Shienzhen.

1.2 Apparatus

MPF-4 spectrofluorometer was made by Hitachi.

logical saline solutions of 20 mL/kg/d were injected; for the positive control group: adriamycin (ADM) 1 mg/kg/d was administered; *Ganoderma lucidum* spores low dose group: 2 g/kg/d; *Ganoderma lucidum* spores medium dose group: 4 g/kg/d/; *Ganoderma lucidum* spores high dose group: 8 g/kg/d. Dosing of the drug was started 24 hours after the inoculation of the ticor cells via savage to the testing animals in each group (the drug was injected intraperitoneally for the ADM group) for 10 consecutive days. The activities, the luster of the skin and fair, and the appearance of the stool of the testing animals in each group were observed. The day after the drug was given for the last time, the mice were sacrificed. They were then weighed, the tumor s re moved and the tumor suppression r ate w as calculated. About 1 g tumor tissue was used to measure the MDA. Excess blood on the tissue was washed with cold 0.9% NaCl. The remaining blood was removed by absorbing the tissue on cloth or paper. The tissue was then cut into pieces and placed in a glass homogenizer; 0.9% NaCl was added, grinding was then carried out to produce a 10% (w/v) homogenized tissue solution. The MDA level in the tumor tissue was measured with the TDA spectrofluorometer.

2. Results 2.1 The tumor suppressing effect of the *Ganoderma lucidum* spores (see Table 1)

For the mouse L-II tumor suppression rate of the *Ganoderma lucidum* spores, the low, medium and high dose groups respectively exhibited 66.8%, 70.9%, and 76.2%. The suppression of the tumor was effective in a dose-dependent manner.

TABLE 1

The effect of Germination Activated Sporoderm-Broken *Ganoderma lucidum* spores on the mouse transplant tumor L-II

| Group | Dose (per day, continuously for 7 days) | No. of animals (Beginning/end) | Body weight Beginning | Body weight End | Body weight Change | Weight of the tumor | Rate of tumor suppression | p value compared to the control group |
|---|---|---|---|---|---|---|---|---|
| 1. Control Group | (20 ml/kg) | 12/12 | 21.08 ± 0.90 | 30.85 ± 2.41 | +9.77 | 2.28 ± 0.61 | — | — |
| 2. ADM | (1 mg/kg) | 12/12 | 21.17 ± 0.83 | 28.67 ± 2.15 | +7.05 | 0.78 ± 0.33 | 66.0 | <0.001 |
| *Ganoderma lucidum* spores | (2 g/kg) | 12/12 | 21.14 ± 0.64 | 30.19 ± 2.16 | +9.05 | 0.76 ± 0.30 | 66.8 | <0.001 |
| *Ganoderma lucidum* spores | (4 g/kg) | 12/12 | 21.08 ± 0.79 | 29.92 ± 1.16 | +8.83 | 0.66 ± 26 | 70.9 | <0.001 |
| *Ganoderma lucidum* spores | (8 g/kg) | 12/12 | 21.17 ± 0.83 | 31.58 ± 2.97 | +10.4 | 0.54 ± 0.24 | 76.2 | <0.001 |

1.3 Principle

Under acid conditions, condensation between 2-thiobarbituric acid-malonyl thiourea (TBA) and malondialdehyde (MDA) produced a red compound which emitted fluorescent light (absorbing light at 515 nm wavelength, emitting fluorescent light at 553 nm). The level of MDA was determined by measuring the fluorescent intensity using the nmPF-4 spectro-flurometer.

1.4 Methods

Under antiseptic conditions, the ascitic mouse L-II cells which had been growing well for 7 days were extracted from the abdominal cavity, diluted with biological saline solution at a ratio of 1:1, then the tumor cell suspension was inoculated subcutaneously into the right axilla of the mouse. Each mouse received an inoculation of 0.2 mL. The inoculated mice were then randomly divided into 5 groups with 12 mice for each group. For the negative control group: Bio- 2.2 The effect of spores on the MDA in the mouse tumor tissues The amount of the MDA in the mouse tumor tissues gradually decreased with an increase in the dosage of *Ganoderma lucidum* spores (see Table 2). The amount of the MDA in each of the dosage groups of *Ganoderma lucidum* spores was significantly different from the control group (p<0.001).

TABLE 2

The effect of Germination Activated Sporoderm-Broken *Ganoderma lucidum* spores on the MDA in the mouse tumor tissues (L-II)

| Daily | No. (of | p value compared |

| Group | dose (continuously for 10 days) | animals) beginning/ end | Level of MDA | to the control group |
|---|---|---|---|---|
| 1. Control Group | (20 ml/kg) | 12/10 | 54.17 ± 22.37 | — |
| 2. ADM | (1 mg/kg) | 12/11 | 57.41 ± 23.82 | >0.05 |
| Ganoderma lucidum spores | (2 g/kg) | 12/10 | 32.47 ± 10.25 | <0.05 |
| Ganoderma lucidum spores | (4 g/kg) | 12/12 | 22.87 ± 10.22 | <0.05 |
| Ganoderma lucidum spores | (8 g/kg) | 12/12 | 17.66 ± 10.38 | <0.0001 |

3. Discussion

Free radicals are highly active substances that are constantly produced in the process of cellular metabolism and can have damaging effect on organisms. They can induce oxidation reactions, cause proteins to crosslink and be damaged, decrease the activity of enzymes, contribute to an abnormal metabolism of the nucleic acid, and cause superoxidation of the polyunsaturated lipids in the biological membranes. The results of free radical attack can lead to damage to the cellular structures and functions as well as the various organs in an organism, thus resulting in aging and multiple pathologies.

MDA is a product of the secondary reduction of lipid peroxidation, that is, a metabolite of lipid peroxidation. It is a compound with two functional groups and can react with compounds that contain amino groups, such as proteins, nucleic acids, cephalins, etc., causing them to cross-link and thus lose their functions, with the result of protein denaturation, loss of enzyme activity, and damage to the DNA. Animal tests show that MDA is also a strong carcinogen which can induce tumors in animals. Measurement of MDA in tumor tissues can directly reflect the extent of lipid peroxidation caused by the tumors.

The active components of the *Ganoderma lucidum* spores include antioxidants, such as *Ganoderma lucidum* polysaccharides, *Ganoderma lucidum* acids, SOD, vitamin E, etc., which may be the basis for the capacity of the *Ganoderma lucidum* spores to resist lipid peroxidation. It can be seen, therefore, that *Ganoderma lucidum* spores play a positive role in scavenging free radicals, protecting organisms, and preventing cancers as well as in the treatment of cancers.

According to Tables 1–2, the ADM group exhibits the highest MDA level in the mouse reticulosarcoma tissues. One of the anticancer mechanisms of ADM is its ability to bind metal ions. However, this also leads to the induction of free radicals formation. In addition, although ADM can inhibit the formation of cancers, it attacks the cardiac muscle mitochondria and membrane at the same time, thus leading to severe cardiac toxicity. The ADM group is followed by the positive control group, indicating that the extent of lipid peroxidation is increased during the growth process of the cancerous cells. The MDA levels of the high, medium and low dosage groups of *Ganoderma lucidum* spores are all significantly lower than those of the two positive and negative control groups. Within the dosage range of 2g/kg/d~8g/kg/d, the amount of MDA is significantly decreased with the increase of the dosage of *Ganoderma lucidum* spores, indicating that *Ganoderma lucidum* spores have a large effect on the prohibition of lipid peroxidation, and at the same time the effect is increased with the increase of the dosage within the dosage range of 2g/kg/d~8g/kg/d. Although free radicals can cause damage to cancerous cells, they also cause damage to the organism while destroying cancerous cells. Based on the results of the present test, it can be seen that *Ganoderma lucidum* and *Ganoderma lucidum* spores have a clear suppressing effect on animal tumors. Also, the fact that the effect of *Ganoderma lucidum* spores on inhibiting the MDA level is dose-dependent indicates that, although *Ganoderma lucidum* spores decrease the free radicals in tumor cells, their ability to suppress tumors is not being affected.

In the test presented above, the drug was administered right after the mice were inoculated with cancerous cells. Also, during the growth process of the cancerous cells, *Ganoderma lucidum* spores were continuously administered to the mice. It is proposed that *Ganoderma lucidum* spores continuously suppress the formation of the free radicals by the tumor cells during their growth, thus suppressing the DNA damage caused by the lipid peroxidation, which is again caused by free radicals. Meanwhile, they can also suppress the destruction done to the surrounding tissues by the tumor cells and prohibit their growth. As a result, the decrease in free radicals induced by *Ganoderma lucidum* spores may be one of the mechanisms of *Ganoderma lucidum* spores in prohibiting tumors.

Experimental Example 2

Immunoregulatory Effect of Pure *Ganoderma lucidum* Spore Capsules

I. Test conditions:

1. Samples: The recommended daily dosage was three times per day, 4 capsules each time, with each capsule weighing 0.3 g, based on an adult of 60 kg, at 0.06 g/kg bodyweight (BW). The concentrations needed for various tests were all prepared by diluting the *Ganoderma lucidum* spores with distilled water.

2. Dosage: There were a cold distilled water control group, and low, medium, and high doses groups. The dosages of the low, medium, and high doses groups were as follows:

Low dose group: 0.06 g/kg BW at approximately the recommended daily dose.

Medium dose group: 0.60 g/kg BW at approximately 10 times the recommended daily dose.

High dose group: 1.80 g/kg BW at approximately 30 times the recommended daily dose.

3. Animals: NIH white mice, 6–8 weeks old, weight 20–22 g, were supplied by the Guangdong Medical Animal Farm with qualification inspection approval No. 97A022. The pellets were supplied by the Guangdong Medical Animal Farm.

4. Laboratory for housing animals: Animals were housed in clean environment and at room temperature 25±2° C., humidity 70–75%.

5. Route of administration: The test substances were given to each animal at a dose of 0.2 mL/10 g daily via gavage.

II. Test methods:

1. Test of Delayed Allergic Reaction of the Animals (by measuring the increase of the thickness of the footpad)

After quarantined for one week under laboratory conditions, 40 mice were randomly divided into 4 groups, with 10 for each group. The test substances were administered to the mice every day for a duration of 4 weeks. Four (4) days before the end of the test, the immunized animals were injected with 0.2 mL 2% (v/v) sheep erythrrocytes intrapertoneally to sensitize the animals. Four (4) days later the thickness of the left rear footpad was measured, then 20% (v/v) sheep erythrocytes (20 µL per mouse) were injected subcutaneously at the same location. Twenty four (24) hours after the injection, the thickness of the left rear footpad was measured three times and a mean value was obtained.

2. Measurement of the mouse serum hemolysin titer (by measuring the blood coagulation)

Forty (40) mice were randomly divided into 4 groups, with 10 for each group. The test substances were administered every day for a duration of 4 weeks. The amount of the samples given was adjusted every week according to the body weight. Four (4) days before the end of the test, the immunized animals were each given injections of 0.2 mL 2% (v/v) sheep erythrocytes intraperitoneally, and 5 days later the eyeballs were extracted to obtain blood samples. The blood serum was stored for later use. The thymus and the spleen were weighed and their ratios to the body weight were calculated.

Coagulation reaction: the blood serum was diluted with biological saline solution at an appropriate ratio in a trace element reaction plate, each 50 μL, then 50 μL of 0.5% sheep erythrocytes were added, placed inside a moist container, covered with a lid and placed in an incubator at 37° C. for 3 hours. The degree of coagulation was observed.

3. Mouse carbon clearance test

Forty (40) mice were randomly divided into 4 groups, with 10 for each group. The test substances were administered every day for a duration of 4 weeks. The amount of the samples given was adjusted every week according to the body weight. On Day 28 when the drug was administered for the last time, India ink diluted at 1:4 was intravenously injected into the tail vein of the mouse at 0.1 mL/10 g body weight. Using a timer, 20 μL of blood were drawn at 2 min and 10 min, from the veins inside the canthus, added to 2 mL of $Na_2CO_3$ solution, then the OD value was measured at 600 nm wavelength using a 721 spectrophotometer using $Na_2CO_3$ solution as control. The mice were then sacrificed, the liver and the spleen were weighed to calculate the phagocytic index.

4. Data processing: Variance analysis was carried out using SAS.

III. Test Results

1. The effect of the germination activated sporoderm-broken Ganoderma lucidum spore capsules (cell wall completely penetrated) on the body weight of the mice is shown in Table 3. The initial, intermediate, and final body weights of the mice of each of the test groups were compared to the control groups for the same periods. The results of Table 3 show no statistically significant differences among the test and control groups, suggesting that the pure Ganoderma lucidum spore capsules with cell wall completely penetrated did not have significant effect on body weights of the mice.

TABLE 3

Effects of Germination Activated Sporoderm-Broken Ganoderma lucidum Spore Capsules (Cell Wall Completely Penetrated) on Body Weights of the Mice

| Group | No. of animals (mice) | Initial Body Weight (g)* | Intermediate body weight (g)* | Final body weight (g)* | Difference between Final and Initial Body Weight (g)* |
|---|---|---|---|---|---|
| Control group | 10 | 23.0 ± 1.15 | 24.9 ± 0.75 | 27.7 ± 0.95 | 4.8 ± 1.24 |
| Low dose | 10 | 22.9 ± 1.23 | 25.2 ± 0.76 | 28.0 ± 1.34 | 5.1 ± 0.82 |
| Medium dose | 10 | 22.9 ± 1.16 | 25.3 ± 0.65 | 28.5 ± 1.42 | 5.3 ± 0.97 |
| High dose | 10 | 23.2 ± 0.96 | 25.3 ± 0.55 | 27.6 ± 1.46 | 4.6 ± 0.71 |
| F value | | 0.18 | 0.76 | 0.89 | 1.15 |
| p value | | >0.05 | >0.05 | >0.05 | >0.05 |

*Values are expressed as Mean ± S.D.

2. The effect of the germination activated sporoderm-broken Ganoderma lucidum spore capsules (cell wall completely penetrated) on the spleen and thymus weights of the mice is shown in Table 4. The ratios of spleen/body weight and thymus/body weight of the mice of each of the test groups were compared to the control groups. The results show no significant difference between the test and the control groups, indicating that pure Ganoderma lucidum spore capsules (cell wall completely penetrated) have no effects on spleen and thymus weights of the mice.

TABLE 4

Effects of Sporoderm-Broken Ganoderma lucidum Spore Capsules (Cell Wall Completely Penetrated) on Spleen and Thymus Weights of the Mice

| Group | No. of animals | Body weight (g) | Thymus/body weight (g) | Spleen/body weight (g) |
|---|---|---|---|---|
| Control group | 10 | 28.7 | 3.52 ± 0.46 | 4.08 ± 0.82 |
| Low dose | 10 | 27.6 | 3.44 ± 0.37 | 3.85 ± 0.38 |
| Medium dose | 10 | 29.3 | 3.18 ± 0.26 | 4.63 ± 0.75 |
| High dose | 10 | 28.9 | 3.21 ± 0.45 | 4.20 ± 0.88 |
| F value | | | 2.02 | 0.43 |
| P value | | | >0.05 | >0.05 |

3. The effect of the germination activated sporoderm-broken Ganoderma lucidum spore capsules (cell wall completely penetrated) on the delayed allergic reaction of the mice is shown in Table 5. The thickness of the footpads of the mice in the low, medium and high dose groups were compared to those of the control group and statistically processed. The results show significant differences between the tested and control groups.

TABLE 5

Effects of the Germination Activated Sporoderm-Broken Ganoderma lucidum Spore Capsules (Cell Wall Completely Penetrated) on the Delayed Allergic Reaction of the Mice

| Group | No. of animals | Thickness (mm) of the left rear footpad (Mean ± S.D.) | p value (compared to the control group) |
|---|---|---|---|
| Control group | 10 | 0.43 ± 0.16 | |
| Low dose | 10 | 0.71 ± 0.22 | <0.01 |
| Medium dose | 10 | 0.68 ± 0.10 | <0.01 |

TABLE 5-continued

Effects of the Germination Activated Sporoderm-Broken
*Ganoderma lucidum* Spore Capsules (Cell Wall Completely Penetrated)
on the Delayed Allergic Reaction of the Mice

| Group | No. of animals | Thickness (mm) of the left rear footpad (Mean ± S.D.) | p value (compared to the control group) |
|---|---|---|---|
| High dose | 10 | 0.77 ± 0.19 | <0.01 |

F value 7.70 (P < 0.01)
Note: p value is the result of q test, and the comparison of each test group with the control groups 4. The effect of the germination activated sporoderm-broken *Ganoderma lucidum* spore capsules (cell wall completely penetrated) on antibody titers of the serum hemolysin of the test animals is shown in Table 6. The results show that only the high dose group was significantly different from the control group, indicating that only at high dose the sporoderm-broken *Ganoderma lucidum* spore capsules (cell wall completely penetrated) have effects on antibody titers of the serum hemolysin.

TABLE 6

Effect of the Germination Activated Sporoderm-Broken
*Ganoderma lucidum* Spore Capsules (Cell Wall Completely Penetrated)
on Antibody Titers of Serum Hemolysin

| Group | No. of Animals | Antibody product Mean | ± | Standard Deviation | p value (compared to the control group) |
|---|---|---|---|---|---|
| Control Group | 10 | 72.6 | ± | 17.59 | |
| Low dose | 10 | 87 | ± | 13.70 | >0.05 |
| Medium dose | 10 | 89.6 | ± | 13.43 | >0.05 |
| High dose | 10 | 103.4 | | 16.19 | <0.01 |

F value 6.78 (p < 0.01)
Note: p value is the result of q test, and the comparison of each test group with the control groups.

5. The effect of the germnuation activated sporoderm-broken *Ganoderma lucidum* spore capsules (cell wall completely penetrated) on the carbon clearance phagocytic index of the mice is shown in Table 7. Only the high dose group shows significant difference as compared to the control group, indicating that at high dose, the germination activated sporoderm-broken *Ganoderma lucidum* spore capsules (cell wall completely penetrated) significantly increase the carbon clearance phagocytic index of the test animals.

TABLE 7

Effects of the Germination Activated Sporoderm-Broken
*Ganoderma lucidum* Spore Capsules (Cell Wall Completely Penetrated)
on the Carbon Clearance Phagocytic Index of Mice

| Group | No. of Animals | Carbon clearance phagocytic index Mean | ± | S.D. | p value (compared to the control group) |
|---|---|---|---|---|---|
| Control Group | 10 | 4.59 | ± | 0.34 | |
| Low dose | 10 | 4.7 | ± | 0.59 | >0.05 |
| Medium dose | 10 | 5.01 | ± | 0.21 | >0.05 |
| High dose | 10 | 5.2 | ± | 0.39 | >0.05 |

F value 4.73 (p < 0.01)
Note: p value is the result of q test, and the comparison of each test group with the control groups.

IV. Conclusion:

By using the germination activated sporoderm-broken *Ganoderma lucidum* spore capsules (cell wall completely penetrated), the delayed allergic reaction of the mice, induced by the sheep erythrocytes, was significantly increased (as measured by the increase in the thickness of the footpad) and the thickness of the footpad was increased, indicating an effect on increasing the immune fimetion of the cells; the antibody titer of the blood serum hemolysin of the animals tested was significantly elevated, indicating an effect on increasing the humoral immune function; and the carbon clearance phagocytic index of the animals tested was significantly increased, indicating an effect on increasing the phagocytosis by the macrophages.

The results also show that the germination activated sporoderm-broken *Ganoderma lucidum* spore capsules (cell wall completely penetrated) exhibit immunoregulatory effects.

Experimental Example 3

Toxicoloy Tests and Tests of Prevention of
Bacterial Infections on Ganoderma in Mice I. Material:

1. Test materials: The germination activated sporoderm-broken ganodenna spores samples appeared as brown powders. After going through a 100 mesh sieve, 120 g of the samples were mixed with 300 mL distilled water and stirred for 15 min in a stirrer at 7000 rpm. They were then bottled, underwent sterilization, and a 0.4 g/mL of a pasty liquid was obtained. Dose was given twice a day via gastric gavage.

2. Animals: Healthy NIH white mice were obtained from Guangdong Medical Animals Farm, with body weights of 18–22 g.

II. Methods and Results:

1. Acute toxicity $LD_{50}$ test:

Forty (40) NIH small white mice with body weights of 18–22 g, half male and half female, were used in this test. The mice were randomly divided into 4 groups. One dose was given via gastric gavage on empty stomach. Observation was carried out for a week and the results are shown in Table 8.

TABLE 8

Acute toxicity test results

| Dose (g/kg) | No. of animals Female | Male | No. of dead animals Female | Male |
|---|---|---|---|---|
| 21.50 | 5 | 5 | 0 | 0 |
| 10.00 | 5 | 5 | 0 | 0 |
| 4.64 | 5 | 5 | 0 | 0 |
| 2.15 | 5 | 5 | 0 | 0 |

Result: The activity and food consumption of the test mice appeared normal. There was no deaths. The oral $LD_{50}$ was >21.5 g/kg BW.

The results demonstrate that the sampled germination activated sporoderm-broken *Ganoderma lucidum* spore capsules (cell wall completely penetrated) was nontoxic. The amount was 268.75 times the recommended treatment amount (0.08 g/kg BW).

2. Bone marrow micronucleus test:

Seventy (70) NIH mice with body weights of 20–23 g were used in this test. The mice were divided into 7 groups and testing was carried out according to the method of the Toxicological Evaluation Procedures for Food Safety. Doses were given twice daily via gastric gavage. Six (6) hours after the second administration the mice were sacrificed, and both of the femurs were taken out for the preparation of slides, staining and examination under a microscope. Ten thousand polychromatic erythrocytes (NCE) were examined. The numbers of micronucleated PCE (MN-PCE) were determined and the results are shown in Table 9.

Result: The micronucleus rate of the various dose groups of the germination activated sporodermn-broken *Ganoderma lucidum* spore capsules (cell wall completely penetrated) was similar to that of the blank control group and none of them showed a significant difference. The test showed a negative result.

TABLE 9

Mouse Bone Marrow Micronucleus Test Result

| Dose (g/kg) | No. of Animals (Male) | No. of Animals (Female) | No. of PCE Examined | No. of MN-PCE | Micronuclei Ratio |
|---|---|---|---|---|---|
| 0 | 5 | 5 | 10000 | 14 | 1.4 |
| 10.00 | 5 | 5 | 10000 | 15 | 1.5 |
| 5.00 | 5 | 5 | 10000 | 14 | 1.4 |
| 2.50 | 5 | 5 | 10000 | 13 | 1.3 |
| 1.25 | 5 | 5 | 10000 | 14 | 1.4 |
| 0.62 | 5 | 5 | 10000 | 12 | 1.2 |
| Cyclo-phosphamide (0.06) | 5 | 5 | 10000 | 249 | 24.9** |

**The blank control group and the various dose groups compared to the positive cyclophosphamide group $p < 0.001$. Two-tail T-test statistical processing was used.

3. Sperm deformation test

Twenty five (25) NIH mice with body weights of 18–22 g were randomly divided into 5 groups and dosed via gastric gavage daily for 5 days (the cyclophosphamide positive group received intraperitoneal injections). Thirty five (35) days later, the animals were sacrificed and both testicles were taken out for the standard slide preparation and staining. Five thousand (5000) whole sperm from each set were examined under an oil immersion lens and the sperm deformation ratio was calculated. The results are shown in Table 10.

TABLE 10

Effect of the Germination Activated Sporoderm-Broken
*Ganoderma lucidum* Spore Capsules
(Cell Wall Completely Penetrated) on Mouse Sperm Deformation

| Dose (g/kg) | No. of animals | No. of Sperm Examined | No. of Deformed Sperms | Deformation Ratio |
|---|---|---|---|---|
| 0 | 5 | 5000 | 98 | 19.60 |
| 10.00 | 5 | 5000 | 98 | 19.60 |
| 5.00 | 5 | 5000 | 94 | 18.80 |
| 2.50 | 5 | 5000 | 92 | 18.40 |
| Cyclophosph-amide (0.04) | 5 | 5000 | 364 | 72.80** |

**The blank control group and the various dose groups compared to the cyclophosphamide group $p < 0.01$.

Result: The sperm deformation ratios of the various dose groups treated with the germination activated sporoderm-broken *Ganoderma lucidum* spore capsules (cell wall completely penetrated) were similar to that of the blank control group. Even when a dose as high as 50.00 g/kg BW was used, no induced deformation of the reproductive cells was found.

4. Ames test

Test bacteria (TA97, TA98, TA100, TA102) were supplied by the Bureau of Food Inspection, Department of Health in Beijing. Characteristics and the S9 activity of the bacteria were evaluated and they met the requirement. Using the Petri dish mixing method, two independent tests were carried out. Three dishes were prepared for each group and the results are shown in Table 11.

Result: Whether or not S9 mixtures were added to each of the dose groups treated with the germination activated sporoderm-broken *Ganoderma lucidum* spore capsules (cell wall completely penetrated), the test results showed that the number of colonies with reverse mutation was never more than 2 times the number of colonies due to natural mutation. There was no indication that the germination activated sporoderm-broken *Ganoderma lucidum* spore capsules (cell wall completely penetrated) could cause mutations directly or indirectly.

TABLE 11

Bacteria Test of the Germination Activated Sporoderm-Broken *Ganoderma lucidum* Spore Capsules Using the Petri Dish Mixing Method

| Dosage | TA97 | | TA98 | | TA100 | | TA102 | |
|---|---|---|---|---|---|---|---|---|
| µg/dish | +S9 | −S9 | +S9 | −S9 | +S9 | −S9 | +S9 | −S9 |
| 5000 | 149 | 135 | 33 | 32 | 180 | 167 | 311 | 296 |
| 500 | 154 | 141 | 37 | 34 | 148 | 152 | 311 | 195 |
| 50 | 161 | 152 | 47 | 36 | 175 | 164 | 305 | 288 |
| 5 | 149 | 153 | 35 | 30 | 167 | 159 | 299 | 267 |
| 0.5 | 164 | 159 | 38 | 35 | 153 | 146 | 305 | 288 |
| Natural reverse mutation | | 142 | | 39 | | 154 | | 297 |
| Positive control | | | | | | | | |
| Atabrine | | >1500 | | >1433 | | | | |
| Sodium azide | | | | | | >1500 | | |
| Mitomycin | | | | | | | | >1500 |
| 2-Aminofluorine | >1500 | | >1600 | | >1500 | | >855 | |

IV. Summary of Test results:
1. $LD_{50}$:

As shown in Table 8, no adverse effects were observed in animals being given germination activated sporoderm-activated *Ganoderma lucidum* spores. The oral $LD_{50}$ was over 21.5 g/kg BW. The results demonstrate that the germination activated sporoderm-broken *Ganoderma lucidum* spores are nontoxic.

2. Micronucleus test

As shown in Table 9, the bone marrow micronucleus test was conducted to study whether germination activated sporoderm-broken *Ganoderma lucidum* spore capsules (cell wall completely penetrated) in the dosage ranging between 0.62 and 10 g/kg BW have effects on cell mutation. Results show no significant differences between the *Ganoderma lucidum* group and the blank control group, indicating that germination activated sporoderm-broken *Ganoderma lucidum* spores did not induce cell mutation in vivo.

3. Sperm deformation test

As shown in Table 10, the sperm deformation rate for animals which were given 2.5–10 g/kg BW of germination activated sporoderm-broken *Ganoderma lucidum* spores was the same as that of the blank control group (statistically insignificant), indicating that the germination activated sporoderm-broken *Ganoderma lucidum* spores did not induce sperm deformation in vivo.

4. Ames test

As shown in Table 11, Germination activated sporoderm-broken *Ganoderma lucidum* spores in the dosage of 0.5–5000 pg/dish did not significantly induce reverse mutation (the test results show that the number of colonies due to reverse mutation was never more than 2 times the number of colonies due to natural mutation). The results also show that germination activated sporoderm-broken *Ganoderma lucidum* spores did not cause mutations directly or indirectly.

Experimental Example 4

Toxicology Tests of Ganoderma in Rats

I. Material:

1. Test material: The samples appeared as brown powders. After going through a 100 mesh sieve, 120 g of the samples were mixed with 300 L distilled water and stirred for 15 min at 7000 rpm. They were then subjected to sterilization treatments for 20 min, and made into pastes. One (1) mL of the paste was about 0.4 g of the samples.

2. Animals: Healthy SD rats supplied by the Guangdong Medical Animals Farm.

II. Methods:

Ninety six (96) homogenous healthy SD rats with body weights of 80–88 g were randomly divided into 4 groups with 24 rats for each group, half male and half female. The average difference in body weight in each of the group was less than ±5 g. Observation was carried out for 1 week before the administration of the drug to see if there were any abnormal activities, feeding or characteristic appearances.

1. Dosage: The recommended treatment dosage for adult humans was 4 times daily, 4 capsules (0.3 g per capsule) each time. This dosage is based upon the assumption that an adult human weighs 60 kg. This dosage can be converted into the dosage of 0.08 g/kg BW. For the animal toxicity testing, three test groups and one control group were set up respectively so that each group contained 12 rats with half of them male and half of them female.

Blank control group: Distilled water
25X group: 2.0 g/kg/day
50X group: 4.0 g/kg/day
100X group: 8.0 g/kg/day 2. Test methods:

(1) The rats were treated via gavage every day with doses calculated according to their body weights for 30 consecutive days. The high dose group was gavaged twice every day and the control group was gavaged the same amount of distilled water. The body weights were taken every week and the amount of the food consumed was detenrined while tracking the physiological indexes of the animals.

(2) Standard blood tests were carried out at the end of the treatment. The blood tests included the erythrocyte counts, hemoglobin, white blood cell and other differential cell counts, and the number of platelets, all were measured by the R-1000SYSME blood cell counter made in Japan. For blood biochemistry, blood sugar, albumin, triglycerides, total cholesterol, creatinine, glutamate-pyruvate transaminase and blood urea nitrogen were tested. Measurements were carried out using the ALIZE automatic biochemical analyzer made in France.

(3) In each animal, the liver, kidney, spleen, heart and testicles were extracted and weighed. These organs were then preserved in formaldehyde. Slides were prepared and stained for pathological observations.

III. Result and analysis:

1. The rats from the different dose groups grew well and there were no significant differences when compared to the control group ($p>0.05$) (See Tables 12 and 13). The food consumption and utilization rate of the food in the dose groups show no significant differences from the control group (See Table 13).

2. In the final blood test, none of the specific indexes showed any significant differences when compared to the control group (See Table 14).

3. In the blood chemistry studies, the blood sugar levels of the male rats were significantly decreased in the low and medium dose groups ($p<0.01$) as well as in the high dose group($p<0.05$), as compared to the control group. The blood sugar levels of the female rats were also significantly reduced in the low dose group ($p<0.01$) as well as in the medium and high dose groups ($p<0.05$), as compared to the control group. However, these values were still within the normal ranges. There were significant differences in the blood urea nitrogen content of the male rats in the low and medium dose groups when compared to the control group ($p<0.05$). There were significant differences in the triglyceride of the female rats in the low and high dose groups when compared to the control group ($p<0.05$). There were no significant differences in the other indexes of any of the test groups when compared to the control group (See Table 15).

4. There were no significant differences in the organ indexes of each of the test groups when compared to the control group (See Table 16). Pathological observation showed that there were no pathological abnormalities of the organs in any of the test groups.

TABLE 12

Increase in Body Weights of the Rats

| Sex | Group* | Original body weight (g)** | Body weight after First week (g)** | Body weight after Second week (g)** | Body weight after Third week (g)** | Body weight after Forth week (g)** |
|---|---|---|---|---|---|---|
| Male rats | Control | 87 ± 9.4 | 120.2 ± 11.0 | 152.1 ± 12.9 | 192.0 ± 13.4 | 242.3 ± 17.6 |
| | 25 Times | 88.0 ± 6.7 | 125.1 ± 9.3 | 145.0 ± 9.9 | 190.6 ± 11.5 | 242.0 ± 18.2 |
| | 50 Times | 85.7 ± 8.6 | 125.8 ± 15.2 | 148.4 ± 12.1 | 192.9 ± 12.2 | 235.5 ± 24.0 |
| | 100 Times | 86.6 ± 8.9 | 123.0 ± 13.7 | 154.7 ± 17.0 | 202.2 ± 18.3 | 251.6 ± 25.8 |
| Female rats | Control | 82.4 ± 7.5 | 109.2 ± 8.0 | 148.8 ± 8.2 | 165.1 ± 14.0 | 202.6 ± 16.1 |
| | 25 Times | 80.5 ± 7.3 | 117.7 ± 9.2 | 144.3 ± 9.9 | 174.2 ± 12.0 | 206.2 ± 11.5 |
| | 50 Times | 80.5 ± 5.9 | 112.4 ± 15.2 | 141.2 ± 9.9 | 171.5 ± 13.1 | 199.6 ± 17.2 |
| | 100 Times | 81.7 ± 6.6 | 115.3 ± 13.0 | 144.1 ± 14.7 | 171.5 ± 16.2 | 206.8 ± 24.9 |
| F Value | Male | 0.15 | 0.48 | 0.75 | 1.33 | 1.27 |
| | Female | 0.21 | 2.73 | 1.01 | 0.94 | 0.45 |

*Each group contains 12 animals.
**Values are expressed as Mean ± SD.

TABLE 13

Increase in Body Weights, Food Consumption and Utilization

| Sex | Group* | Initial body weight (g)** | Final Body weight (g)** | Increase in the body weight (g) | Amount of food consumed (g/mouse) | Utilization of food |
|---|---|---|---|---|---|---|
| Male rats | Control | 87 ± 9.4 | 242.3 ± 17.6 | 155.2 ± 20.1 | 596.4 | 26.02 |
| | 25 Times | 88.0 ± 6.7 | 242.0 ± 18.2 | 154.0 ± 15.5 | 656.7 | 23.45 |
| | 50 Times | 85.7 ± 8.6 | 235.5 ± 24.0 | 149.8 ± 24.3 | 625.6 | 23.95 |
| | 100 Times | 86.5 ± 8.9 | 251.6 ± 25.8 | 165.1 ± 19.5 | 640.9 | 25.76 |
| Female rats | Control | 82.4 ± 7.5 | 201.6 ± 16.1 | 119.2 ± 19.5 | 552.8 | 21.56 |
| | 25 Times | 80.5 ± 7.3 | 206.2 ± 11.5 | 125.7 ± 11.8 | 574.8 | 21.87 |
| | 50 Times | 80.5 ± 5.9 | 199.6 ± 17.2 | 119.1 ± 14.7 | 569.2 | 20.92 |
| | 100 Times | 81.7 ± 6.6 | 206.8 ± 24.9 | 125.1 ± 25.5 | 565.7 | 22.11 |
| Net increase in body weight of the male rats | F = 1.27 | P > 0.05 | Net increase in body weight of the female rats | F = 1.12 | P > 0.05 | |

*Each group contains 12 animals.
**Mean ± SD.

TABLE 14

Standard Blood Indexes

| | Group* | Red Blood Cells (× $10^{12}$/L) | Hemoglobin (g/L)** | Blood platelets (× $10^{19}$/L)** | White blood cells (× $10^9$/L)** | Lymphocytes (%)** | Other white cells (%)** | Neutrophils (%)** |
|---|---|---|---|---|---|---|---|---|
| Male rats | Control | 6.84 ± 0.36 | 124.2 ± 10.1 | 1063.2 ± 167.4 | 7.17 ± 1.23 | 90.4 ± 5.4 | 5.5 ± 3.2 | 4.1 ± 2.4 |
| | 25 Times | 6.57 ± 0.51 | 122.2 ± 13.8 | 931.8 ± 90.9 | 10.85 ± 3.53 | 90.9 ± 3.8 | 4.3 ± 1.7 | 4.8 ± 2.5 |
| | 50 Times | 6.51 ± 0.41 | 122.5 ± 14.1 | 981.7 ± 190.3 | 9.40 ± 1.86 | 90.6 ± 3.9 | 4.8 ± 1.7 | 4.6 ± 2.7 |
| | 100 Times | 6.71 ± 0.38 | 123.2 ± 10.6 | 1169.8 ± 254.2 | 8.12 ± 2.00 | 91.3 ± 2.5 | 4.8 ± 1.4 | 3.9 ± 1.6 |
| Fem. rats | Control | 6.74 ± 0.66 | 132.0 ± 10.1 | 1155.7 ± 196.3 | 9.63 ± 3.39 | 91.3 ± 4.7 | 4.3 ± 2.0 | 4.4 ± 2.8 |
| | 25 Times | 6.32 ± 0.62 | 126.1 ± 2.9 | 1202.5 ± 256.6 | 10.68 ± 2.89 | 93.6 ± 2.8 | 3.9 ± 1.6 | 3.7 ± 1.2 |
| | 50 Times | 6.43 ± 0.91 | 133.2 ± 9.2 | 1241.8 ± 199.6 | 8.73 ± 1.79 | 90.3 ± 4.4 | 4.8 ± 1.8 | 4.8 ± 3.2 |
| | 100 Times | 6.33 ± 0.50 | 127.8 ± 7.7 | 1440.2 ± 377.5 | 10.42 ± 1.19 | 92.2 ± 4.2 | 4.1 ± 1.9 | 3.8 ± 2.4 |
| White blood cells | | F = 5.14 | | P < 0.01 | | Compared to the control group | | P < 0.05 |

*Each group contains 12 animals.
**Values are expressed as Mean ± SD.

TABLE 15

Blood Chemistry

| | Group* | Blood sugar (mmol/L) | Triglycerides (mmol/L) | Total cholesterol (mmol/L) | Blood urea nitrogen (mmol/L) | Glutamate pyruvate transaminase (IU/L) | Serum albumin (g/L) | Creatinine (mmol/L) |
|---|---|---|---|---|---|---|---|---|
| Male rats | Control | 3.71 ± 0.59 | 1.41 ± 0.37 | 1.78 ± 0.23 | 10.29 ± 1.61 | 51.0 ± 7.6 | 38.09 ± 1.42 | 66.76 ± 4.91 |
| | 25 Times | 2.65 ± 0.67 | 1.67 ± 0.44 | 1.98 ± 0.30 | 8.64 ± 1.32 | 55.8 ± 10.5 | 40.73 ± 1.72 | 65.57 ± 6.52 |
| | 50 Times | 2.75 ± 0.41 | 1.63 ± 0.42 | 1.90 ± 0.41 | 8.40 ± 1.58 | 55.8 ± 11.7 | 41.42 ± 1.39 | 66.57 ± 5.52 |
| | 100 Times | 3.08 ± 0.48 | 1.36 ± 0.39 | 1.73 ± 0.36 | 9.44 ± 2.07 | 59.1 ± 10.9 | 40.91 ± 0.91 | 67.56 ± 4.91 |
| Female Rats | Control | 4.92 ± 0.63 | 0.79 ± 0.18 | 1.83 ± 0.29 | 8.88 ± 1.50 | 48.0 ± 8.3 | 40.72 ± 0.96 | 70.60 ± 6.26 |
| | 25 Times | 3.75 ± 0.59 | 1.10 ± 0.25 | 1.94 ± 0.28 | 9.24 ± 0.95 | 53.8 ± 11.9 | 40.28 ± 1.44 | 70.33 ± 4.23 |
| | 50 Times | 4.24 ± 0.37 | 0.92 ± 0.20 | 1.78 ± 0.22 | 9.99 ± 1.42 | 54.1 ± 6.9 | 41.69 ± 1.38 | 73.98 ± 6.14 |
| | 100 Times | 4.27 ± 0.55 | 1.02 ± 0.23 | 1.99 ± 0.39 | 8.95 ± 2.07 | 51.6 ± 13.2 | 41.85 ± 2.56 | 74.84 ± 7.81 |
| | F value Male 7.08 | 0.05 | 1.32 | 4.49 | 1.26 | 0.78 | 0.28 |
| | Female 9.60 | 4.59 | 1.19 | 1.3 | 0.03 | 2.42 | 1.64 |

*Each group contains 12 animals.
**Values are expressed as Mean ± SD.

TABLE 16

Organ Indexes

| | Group* | Heart (g)** | Liver (g)** | Spleen (g)** | Kidney (g)** | Testicles (g)** |
|---|---|---|---|---|---|---|
| Male rats | Control | 0.31 ± 0.03 | 2.67 ± 0.18 | 0.24 ± 0.03 | 0.63 ± 0.05 | 0.86 ± 0.09 |
| | 25 Times | 0.31 ± 0.03 | 2.60 ± 0.18 | 0.26 ± 0.05 | 0.64 ± 0.04 | 0.82 ± 0.12 |
| | 50 Times | 0.30 ± 0.03 | 2.60 ± 0.45 | 0.24 ± 0.05 | 0.65 ± 0.07 | 0.87 ± 0.14 |
| | 100 Times | 0.31 ± 0.03 | 2.65 ± 0.17 | 0.21 ± 0.02 | 0.63 ± 0.05 | 0.86 ± 0.08 |
| Female rats | Control | 0.32 ± 0.02 | 2.44 ± 0.23 | 0.26 ± 0.05 | 0.63 ± 0.10 | |
| | 25 Times | 0.31 ± 0.03 | 2.47 ± 0.72 | 0.27 ± 0.03 | 0.64 ± 0.06 | |
| | 50 Times | 0.33 ± 0.04 | 2.24 ± 0.78 | 0.25 ± 0.78 | 0.67 ± 0.08 | |
| | 100 Times | 0.33 ± 0.03 | 2.45 ± 0.34 | 0.25 ± 0.05 | 0.64 ± 0.07 | |

*Each group contains 12 animals.
*Each group contains 12 animals.
**Values are expressed as Mean ± SD.

IV. Summary of Test Results

In the present test, 25, 50 and 100 times the recommended amount (0.08 g/kg BW) of the germination activated sporoderm-broken *Ganoderma lucidum* spore capsules (cell wall completely penetrated) were administered to growing SD rats of both male and female. The control group was given distilled water. The duration of the test lasted for 30 days and the final results were:

1. Compared to the control group, there was no significant difference in the increase in body weight of the test rats given the pure *Ganoderma lucidum* spores.
2. The standard blood test showed a basically normal result.
3. The blood chemistry there was a slight decrease in the blood sugar, a slight increase in the triglycerides for the female but these were within the normal range.
4. Examination of the pathological biopsies of the organs of the rats from each of the dose groups showed no abnormalities.

Conclusions: Examination of the 30 days feeding with the germination activated sporoderm-broken *Ganoderma lucidum* spore capsules (cell wall completely penetrated) showed that all the indexes were normal, and they could be safely used.

Exerimental Example 5

Antitumor Activity of Germination Activated Sporoderm-broken Ganoderma Spores

I. Objective

The objective of this study is to investigate in vivo antitumor effects of germination activated ganoderma spore on inoculated animal solid tumors such as mouse hepatoma, mouse sarcoma 180 (S-180) and mouse reticulocyte sarcoma (L-II).

II. Methods:

Experimental NIH mice, 20–22 g weight and equal numbers of females and males, were obtained from Experimental Animal Center, Public Hygiene Office of Guangdong Province, China. The strains for mouse sarcoma 180 (S-180), mouse hepatoma, and mouse reticulocyte sarcoma (L-II) were from Cancer Institute, Sun Yat-sen University of Medical Sciences, Guangzhou, China. The germination activated ganoderma spore suspensions (0.2 g/ml) were provided according to the present invention by Guangzhou Green Food Engineering Co. Ltd. and Green Power Health Products International Co. Ltd. (Hong Kong). Cyclophosphamide (CTX) were purchased from $12^{th}$ Medicine Factory, Shanghai. Adriamycin was purchased from Shenzhen Wong Don Pharmaceutical Company.

Mouse sarcoma 180 (S-180), mouse hepatoma, and mouse reticulocyte sarcoma (L-II) cells were extracted and diluted with physiological saline under aseptic condition. The right armpit of each mouse was inoculated with 0.2 ml ($1\times10^7$ cells) of tumor cell suspensions. The inoculated mice were randomly divided into five groups (10~2 rats per group): (1) negative control group (animals were given saline [20 ml/kg/d]); (2) positive control group (animals were given cyclophosphamide [20 mg/kg/d]); (3) low dose of ganoderma spore group (2 g/kg/d); (4) medium dose group (4 g/kg/d); and (5) high dose of group (8 g/kg/d). Treatment was initiated 24 hours after inoculation for a duration of seven days. For low and medium dose groups, drug was given via gavage one time every morning. For high dose group, drug was given via gavage one time in the morning and another in the afternoon. The movement, coat glossiness, and stools of mice were observed. Then the mice were sacrificed by cervical dislocation on the eighth day and weighed with an electric balance. The tumor in the armpit was excised and weighed. The antitumor effect was evaluated by the tumor inhibitory rate:

The tumor inhibitory rate (IR %)=[1−(Average tumor weight of the treatment group/Average tumor weight of the control group)]×100%

The t-test was employed to compare the difference between the treatment group and the control group.

III. Results:

A. Inhibitory effect of germination activated ganoderma spore on mouse sarcoma 180 (S-180).

The experimental results are displayed in Table 17. The antitumor inhibitory (three replications) for 2 g/kg//d of ganoderma spore group was 42.3~45.2%; the tumor inhibitory rate (three replications) for 4 g/kg/d of ganoderma spore group was 56.2~57.3%; the tumor inhibitory rate (three replications) for 8 g/kg/d/ of ganoderma spore group was 79.3~82.0%. The t-test shows that the difference between the average tumor weight for the groups treated with ganoderma spores and the average tumor weight for the negative control group was significant (p<0.001). Moreover, after taking the ganoderma spores, the experimental mice gained weight dramatically and were in good conditions without side effects such as hair lost and diarrhea.

TABLE 17

The Inhibitory Effect of Germination Activated *Ganoderma lucidum* Spores on Mouse Sarcoma 80 (S-1 80)

| Group | Dose/day (7 days) | No. of animal begin/end | Weight (g)* Begin | Weight (g)* End | Changes | Tumor Weight (g)* | Anti-tumor (%) | P |
|---|---|---|---|---|---|---|---|---|
| Control | 20 ml/kg | 10/10 | 20.80 ± 0.60 | 26.10 ± 0.50 | +5.30 | 2.01 ± 0.31 | | |
| CTX | 20 mg/kg | 10/10 | 21.02 ± 0.50 | 24.30 ± 0.40 | +3.28 | 0.80 ± 0.22 | 60.2 | <0.001 |
| GS | 2 g/kg | 10/10 | 21.01 ± 0.40 | 26.61 ± 0.31 | +5.50 | 1.16 ± 0.23 | 42.3 | <0.001 |
| GS | 4 g/kg | 10/10 | 21.02 ± 0.50 | 26.63 ± 0.20 | +5.51 | 0.87 ± 0.24 | 56.2 | <0.001 |
| GS | 8 g/kg | 10/10 | 21.20 ± 0.30 | 27.35 ± 0.35 | +6.15 | 0.40 ± 0.22 | 79.3 | <0.001 |
| Control | 20 ml/kg | 10/10 | 20.75 ± 0.80 | 25.08 ± 0.84 | +4.33 | 2.17 ± 0.42 | | |
| CTX | 20 mg/kg | 10/10 | 21.25 ± 0.80 | 24.65 ± 1.10 | +3.40 | 0.86 ± 0.21 | 60.4 | <0.001 |
| GS | 2 g/kg | 10/10 | 21.05 ± 0.70 | 25.26 ± 0.95 | +4.21 | 1.20 ± 0.23 | 44.9 | <0.001 |
| GS | 4 g/kg | 10/10 | 21.25 ± 0.50 | 25.57 ± 1.16 | +4.32 | 0.94 ± 0.24 | 56.9 | <0.001 |
| GS | 8 g/kg | 10/10 | 21.35 ± 0.60 | 26.42 ± 1.20 | +5.07 | 0.39 ± 0.12 | 82.0 | <0.001 |
| Control | 20 ml/kg | 10/10 | 20.65 ± 0.60 | 25.30 ± 0.44 | +4.65 | 2.17 ± 0.42 | | |
| CTX | 20 mg/kg | 10/10 | 21.30 ± 0.70 | 24.33 ± 0.80 | +3.03 | 0.87 ± 0.24 | 60.1 | <0.001 |
| GS | 2 g/kg | 10/10 | 21.05 ± 0.70 | 26.19 ± 0.97 | +5.14 | 1.19 ± 0.13 | 45.2 | <0.001 |
| GS | 4 g/kg | 10/10 | 21.35 ± 0.40 | 25.84 ± 1.03 | +4.49 | 0.93 ± 0.21 | 57.3 | <0.001 |
| GS | 8 g/kg | 10/10 | 21.40 ± 0.60 | 27.28 ± 0.81 | +5.88 | 0.39 ± 0.12 | 82.0 | <0.001 |

CTX—cyclophosphamide, GS—ganoderma spores
*Values are expressed as Mean ± S.D.

B. The inhibition of gemiination activating ganoderma spore on mouse hepatoma.

Table 18 demonstrates that the tumor inhibitory rate (three replications for 2 g/kg/d of ganoderma spore group was 52.2~74.5%; the tumor inhibitory rate (three replications) for 4 g/kg/d of ganoderma spore group was 63.7~77.7%; the tumor inhibitory rate (three replications) for 8 g/kg/d of ganoderma spore group was 73.2~86.1%. The t-test shows that the difference between the average tumor weight for the groups treated with ganoderma spore and the average tumor weight for the negative control group is significant (p<0.01~0.001).

TABLE 18

The Inhibitory Effect of Germination Activated Ganoderma Spores on Mouse Hepatoma

| Group | Dose/day (7 days) | No. of animal begin/end | Weight (g)* Begin | Weight (g)* End | Change | Tumor weight (g)* | Anti-tumor (%) | P |
|---|---|---|---|---|---|---|---|---|
| Control | 20 ml/kg | 10/10 | 21.43 ± 1.11 | 30.66 ± 3.76 | +9.23 | 1.46 ± 0.33 | | |
| CTX | 20 mg/kg | 10/10 | 21.68 ± 1.05 | 26.72 ± 2.09 | +5.04 | 0.22 ± 0.12 | 84.8 | <0.01 |
| GS | 2 g/kg | 10/10 | 20.50 ± 0.50 | 38.61 ± 1.90 | +8.11 | 0.66 ± 0.14 | 54.7 | <0.01 |
| GS | 4 g/kg | 10/10 | 20.78 ± 0.84 | 26.67 ± 2.83 | +5.89 | 0.37 ± 0.22 | 74.5 | <0.001 |
| GS | 8 g/kg | 10/10 | 20.85 ± 0.75 | 26.71 ± 1.84 | +5.86 | 0.20 ± 0.13 | 86.1 | <0.01 |
| Control | 20 ml/kg | 10/9 | 21.88 ± 1.17 | 34.73 ± 4.99 | +12.90 | 2.34 ± 0.61 | | — |
| CTX | 20 mg/kg | 10/10 | 21.71 ± 1.05 | 31.49 ± 4.39 | +9.78 | 0.66 ± 0.24 | 71.7 | <0.01 |
| GS | 2 g/kg | 10/10 | 22.07 ± 1.03 | 30.54 ± 3.38 | +8.47 | 0.74 ± 0.23 | 62.8 | <0.01 |
| GS | 4 g/kg | 10/10 | 21.87 ± 1.03 | 31.16 ± 3.07 | +9.92 | 0.52 ± 0.12 | 77.7 | <0.01 |
| GS | 8 g/kg | 10/9 | 21.90 ± 0.90 | 30.94 ± 2.38 | +9.00 | 0.44 ± 0.24 | 81.04 | <0.01 |
| Control | 20 ml/kg | 12/12 | 22.11 ± 1.04 | 29.00 ± 2.00 | +6.89 | 1.57 ± 0.22 | | — |
| CTX | 20 mg/kg | 12/12 | 22.09 ± 1.1 | 28.84 ± 2.27 | +6.75 | 0.46 ± 0.14 | 70.7 | <0.01 |
| GS | 2 g/kg | 12/12 | 22.21 ± 1.2 | 30.37 ± 2.73 | +8.16 | 0.75 ± 0.61 | 52.2 | <0.01 |
| GS | 4 g/kg | 12/12 | 22.13 ± 1.4 | 29.38 ± 2.58 | +7.70 | 0.57 ± 0.23 | 63.7 | <0.001 |
| GS | 8 g/kg | 12/12 | 22.2 ± 1.15 | 29.96 ± 2.86 | +7.76 | 0.42 ± 0.22 | 73.2 | <0.001 |

CTX—cyclophosphamide, GS—ganoderma spores
*Values are expressed as Mean ± S.D.

C. The inhibition of germination activated ganoderma spore on mouse reticulocyte sarcoma (L-II).

As shown in Table 19, the tumor inhibitory rate (three replications) for 2 g/kg/d of ganoderma spore group was 54.9~66.8%; the tumor inhibitory rate (three replications) for 4 g/kg/d of ganoderma spore group was 66.9~70.9%; the tumor inhibitory rate (three replications) for 8 g/kg/d of ganoderma spore group was 76.2~79.6%. The t-test shows that the difference between the average tumor weight for the groups treated with ganoderma spore and the average tumor weight for the negative control group was significant ($p<0.001$).

TABLE 19

The Inhibitory Effect of Germination Activated Ganoderma Spores on Mouse Reticulocyte Sarcoma (L-II)

| Group | dose/day (7 days) | No. of animal Begin/end | Weight (g)* Begin | Weight (g)* End | Change | Tumor Weight (g)* | Anti-tumor (%) | P |
|---|---|---|---|---|---|---|---|---|
| Control | 20 ml/kg | 10/10 | 20.89 ± 1.01 | 30.46 ± 1.86 | +9.61 | 0.21 ± 0.41 | — | — |
| ADM | 1 mg/kg | 10/10 | 20.88 ± 1.03 | 27.83 ± 1.84 | +7.04 | 0.78 ± 0.26 | 64.7 | <0.001 |
| GS | 2 g/kg | 10/10 | 20.88 ± 1.04 | 30.62 ± 1.47 | +9.68 | 0.97 ± 0.08 | 56.1 | <0.001 |
| GS | 4 g/kg | 10/10 | 20.88 ± 1.04 | 30.73 ± 1.08 | +9.82 | 0.67 ± 0.12 | 69.9 | <0.001 |
| GS | 8 g/kg | 10/10 | 20.88 ± 1.04 | 32.51 ± 1.93 | +11.60 | 0.45 ± 0.33 | 79.6 | <0.001 |
| Control | 20 ml/kg | 12/12 | 21.08 ± 0.90 | 30.85 ± 2.41 | +9.77 | 2.28 ± 0.61 | — | — |
| ADM | 1 mg/kg | 12/12 | 21.17 ± 0.83 | 28.67 ± 2.15 | +7.05 | 0.78 ± 0.33 | 66.0 | <0.001 |
| GS | 2 g/kg | 12/12 | 21.14 ± 0.65 | 30.19 ± 2.16 | +9.05 | 0.76 ± 0.30 | 66.8 | <0.001 |
| GS | 4 g/kg | 12/12 | 21.08 ± 0.79 | 29.92 ± 1.16 | +8.83 | 0.66 ± 0.26 | 70.9 | <0.001 |
| GS | 8 g/kg | 12/12 | 21.17 ± 0.83 | 31.58 ± 2.97 | +10.4 | 0.54 ± 0.24 | 76.2 | <0.001 |
| Control | 20 ml/kg | 12/12 | 22.42 ± 0.51 | 29.22 ± 2.64 | +6.80 | 1.72 ± 0.44 | — | — |
| ADM | 1 mg/kg | 12/12 | 22.44 ± 0.61 | 27.74 ± 0.74 | +5.30 | 0.74 ± 0.26 | 56.8 | <0.001 |
| GS | 2 g/kg | 12/12 | 22.38 ± 0.59 | 28.55 ± 3.36 | +6.17 | 0.79 ± 0.31 | 54.0 | <0.001 |
| GS | 4 g/kg | 12/12 | 22.34 ± 0.39 | 30.64 ± 3.21 | +8.30 | 0.50 ± 0.17 | 70.9 | <0.001 |
| GS | 8 g/kg | 12/12 | 22.55 ± 0.89 | 29.53 ± 4.41 | +6.98 | 0.36 ± 0.20 | 79.4 | <0.001 |

ADM—adriamycin
GS—ganoderma spores
*Values are expressed as Mean ± S.D.

IV. Conclusions:

The results of Tables 17–19 demonstrate that germination activated ganoderma spores have significant inhibition effects on transplanted animal solid tumors such as mouse hepatoma, mouse sarcoma 180(S-180) and mouse reticulocyte sarcoma (L-II). It is reasonable to expect similar effects on tumors in humans. It is suggested that the germination activated ganoderma spores promote and activate the body's homeostasis response and help to regulate the hormones and receptors in metabolism, neuroendocrine and immune systems, hence to modulate, consolidate and strengthen the body's resistance to diseases.

Experimlental Example 6
Comparative Studies of the Antitumor Effects Between Non-sporoderm Broken and Sporoderm-broken Ganoderma Spores I. Objective:

The objective of the following experiments is to investigate the antitumor effects of non-sporoderm-broken and sporoderm-broken ganodenna spores on transplanted hepatoma in mice.

II. Materials and methods:

The experimental NIH mice, 18–22 g in weight and equal numbers of females and males were purchased from the Experimental Animal Center, Public Hygiene Office of Guangdong Province, China. The mice hepatoma strains were from the Cancer Institute, Sun Yat-Sen University of Medical Sciences. The sporoderm-broken and non sporoderm-broken ganoderma spores were provided by Guangzhou Green Food Engineering Co. and Green Power Health Products Int'l Co., Ltd.

The mouse hepatoma cells, kept in the abdominal cavity for seven days were extracted and diluted with physiological saline solution under aseptic condition. Under asepsis, 0.2 ml of tumor cells suspension ($1 \times 10^7$ cells) were subcutaneously inoculated into the right armpit of mice. The mice were randomly divided into eight groups: (1) negative control group; (2) positive control group; (3) low dose of non-sporoderm-broken group; (4) medium dose of non-sporoderm-broken group; (5) high dose of non-sporoderm-broken group; (6) low dose of sporoderm-broken group; (7) medium dose of sporoderm-broken group; and (8) high dose of sporoderm-broken group. Each group contained 10 mice. Twenty four (24) hours after inoculation, ganoderma spores were given via gastric gavage for seven days. The positive control animals received cyclophosphamide (CTX). The dosage used in each group is illustrated below:

| Treatments | |
|---|---|
| Negative control group (saline): | 20 ml/kg/d |
| Positive control group: | 20 mg/kg/d |
| Ganoderma Spores groups | |
| Low dose group | 2 g/kg/d |
| Medium dose group | 4 g/kg/d |
| High dose group | 8 g/kg/d |

For the low and medium dose groups, the experimental and control suspensions were given in the morning, for high dose group, the suspensions were given once in the morning and once in the afternoon. This continued for seven days. During this period the animals were observed for their movements, stools, and coats. The mice were then sacrificed by cervical dislocation on the eighth day. Their weights were determined with an electric balance. The tumors were exposed, excised and weighed. The tumor inhibitory rate was evaluated, calculations were performed as above.

The entire experiment was repeated three times. The t-test was employed to compare the differences among the groups.

III. Results:

A. Tumor inhibition rate for the non-sporoderm broken ganoderma spores: (see Table 20).

Low Dose Group=6.1%, 8.2% and 6.0% (three replications)

Medium Dose Group=18.2%, 20.8% and 22.6% (three replications)

High Dose Group=−4.8%, 3.1% and 2.4% (three replications)

The tumor inhibition rate was highest in the medium dose group and lowest in the high dose group. Statistical analysis with t-test showed a significant difference $p<0.05$ only within the medium group but not the high or low dose group ($p>0.05$).

B. Tumor inhibition rate for the sporoderm-broken ganoderma spores: (See Table 20).

Low Dose Group=27.1%, 30.2% and 33.3% (three replications)

Medium Dose Group=38.2%, 39.6% and 42.3% (three replications)

High Dose Group=43.3%, 45.3% and 45.8% (three replications)

Statistical analysis with t-test showed significant differences on tumor weight between the experimental groups and the negative control group. Also, during the entire experimental period, no toxic side effects were observed. The movement, stools, and coat of the mice were all normal and no mice died during this period.

TABLE 20

Tumor Inhibition by Non Sporoderm-Broken and Sporoderm-Broken Ganoderma Spores

| Group | Dose/day (7 days) | No. of animal Begin/end | weight (g)* begin | weight (g)* end | Changes | Tumor weight (g)* | Anti-tumor (%) | P |
|---|---|---|---|---|---|---|---|---|
| 1. Control group | 20 ml/kg | 10/10 | 20.48 ± 0.92 | 27.78 ± 3.00 | +7.30 | 1.57 ± 0.2 | — | — |
| 2. CTX | 20 mg/kg | 10/10 | 20.50 ± 1.06 | 25.92 ± 4.09 | +5.40 | 0.53 ± 0.2 | 66.6 | <0.001 |
| 3. GS (N) | Low dose | 10/10 | 20.43 ± 0.80 | 27.11 ± 2.36 | +6.70 | 1.48 ± 0.3 | 6.10 | >0.05 |
| 4. GS (N) | Medium dose | 10/10 | 20.33 ± 0.95 | 28.17 ± 2.54 | +7.80 | 1.29 ± 0.3 | 18.2 | <0.05 |
| 5. GS (N) | High dose | 10/10 | 20.74 ± 0.88 | 27.51 ± 2.01 | +6.80 | 1.65 ± 0.4 | −4.80 | >0.05 |
| 6. GS (B) | Low dose | 10/10 | 20.52 ± 0.94 | 28.88 ± 2.56 | +8.36 | 1.15 ± 0.3 | 27.1 | <0.01 |
| 7. GS (B) | Medium dose | 10/10 | 20.69 ± 1.14 | 29.53 ± 2.69 | +8.80 | 0.97 ± 0.1 | 38.2 | <0.001 |
| 8. GS (B) | High dose | 10/10 | 20.48 ± 0.99 | 28.01 ± 2.09 | +7.50 | 0.89 ± 0.3 | 43.3 | <0.001 |
| 1. Control group | 20 ml/kg | 10/10 | 20.21 ± 0.31 | 27.82 ± 2.89 | +7.61 | 1.59 ± 0.2 | — | — |
| 2. CTX | 20 mg/kg | 10/10 | 20.23 ± 0.24 | 25.42 ± 3.82 | +5.19 | 0.54 ± 0.1 | 66.0 | <0.001 |
| 3. GS (N) | Low dose | 10/10 | 20.24 ± 0.34 | 28.01 ± 2.22 | +7.77 | 1.46 ± 0.2 | 8.20 | >0.05 |
| 4. GS (N) | Medium dose | 10/10 | 20.25 ± 0.36 | 28.21 ± 0.41 | +7.96 | 1.26 ± 0.2 | 20.8 | <0.05 |
| 5. GS (N) | High dose | 10/10 | 20.24 ± 0.35 | 27.81 ± 2.32 | +7.57 | 1.54 ± 0.3 | 3.10 | >0.05 |
| 6. GS (B) | Low dose | 10/10 | 20.23 ± 0.53 | 28.68 ± 2.32 | +8.45 | 1.11 ± 0.2 | 30.2 | <0.01 |
| 7. GS (B) | Medium dose | 10/10 | 20.23 ± 0.54 | 28.90 ± 0.40 | +8.67 | 0.95 ± 0.1 | 39.6 | <0.001 |
| 8. GS (B) | High dose | 10/10 | 20.24 ± 0.55 | 28.12 ± 2.10 | +7.88 | 0.87 ± 0.2 | 45.3 | <0.001 |
| 1. Control group | 20 ml/kg | 10/10 | 20.20 ± 1.22 | 28.20 ± 3.48 | +8.00 | 1.68 ± 0.2 | — | — |
| 2. CTX | 20 mg/kg | 10/10 | 20.24 ± 1.34 | 25.71 ± 2.10 | +5.47 | 0.58 ± 0.1 | 65.5 | <0.001 |
| 3. GS (N) | Low dose | 10/10 | 20.50 ± 1.21 | 27.30 ± 3.28 | +7.19 | 1.58 ± 0.21 | 6.00 | >0.05 |
| 4. GS (N) | Medium dose | 10/10 | 20.12 ± 1.31 | 27.31 ± 2.50 | +7.80 | 1.30 ± 0.1 | 22.6 | <0.05 |

TABLE 20-continued

Tumor Inhibition by Non Sporoderm-Broken and Sporoderm-Broken Ganoderma Spores

| Group | Dose/day (7 days) | No. of animal Begin/end | weight (g)* begin | weight (g)* end | Changes | Tumor weight (g)* | Anti-tumor (%) | P |
|---|---|---|---|---|---|---|---|---|
| 5. GS (N) | High dose | 10/10 | 20.32 ± 1.21 | 28.32 ± 2.20 | +6.81 | 1.64 ± 0.1 | 2.40 | >0.05 |
| 6. GS (B) | Low dose | 10/10 | 20.31 ± 1.20 | 28.11 ± 1.40 | +7.80 | 1.15 ± 0.1 | 33.3 | <0.01 |
| 7. GS (B) | Medium dose | 10/10 | 20.41 ± 1.20 | 28.21 ± 2.50 | +7.80 | 0.97 ± 0.2 | 42.3 | <0.001 |
| 8. GS (B) | High dose | 10/10 | 20.41 ± 1.20 | 28.32 ± 2.28 | +7.91 | 0.91 ± 0.1 | 45.8 | <0.001 |

GS (N)—non-sporoderm-broken spores
GS (B)—sporoderm-broken spores
CTX—cyclophosphamide
*Values are expressed as Mean ± S.D.

As shown in Table 20, non-sporoderm-broken ganoderma spores showed tumor inhibition rate from −4.8 to 22.6% (dose 2 g/kg/d–8 g/kg/d), which is much lower than that of the sporoderm-broken ganoderma spores (i.e., 27.1 to 45.8% inhibition rate). The results shown in Table 20 prove that the sporoderm-broken ganoderma spores display much greater therapeutic effects on tumor inhibition than the non-sporoderm-broken ganoderma spores.

IV. Discussions:

The above studies demonstrate that sporoderm-broken ganoderma spores show a much greater antitumor effect than the non sporoderm-broken ones. One explanation for the differences in antitumor effect can be that the hard sporoderm layers are not easily digestible by humans (antitumor rate −4.8%–22%). But if the sporoderm is broken, the active materials contained can readily be absorbed (antitumor rate 27.1%–45.8%). Also, by synchronizing the germination activation process to induce the maximum production of the bioactive substances, the germination activated ganoderma spores provide more bioactive substances than normal sporoderm-broken ganoderma spores. These bioactive substances demonstrate significantly greater therapeutic effects on diseases than normal sporoderm-broken ganoderma spores.

CLINICAL EXAMPLES

Clinical Exarmple 1

The Effects of Germination-activated Sporoderm-broken Ganoderma Spores on Chronic Hepatitis B (HBV) Patients I. Materials:

Germination-activated sporoderm-broken ganodenna spores were manufactured according to the method of the present invention by Guangzhou Green Food Engineering Co. Ltd. and Green Power Health Products Int'l Co. Ltd.

II. Selection of Patients:

The clinical studies were conducted between December, 1998 and April, 1999. Fourteen (14) patients diagnosed with HBV infection were selected. The selection were based upon the standard criteria set forth in the 1995 National Meeting for the Department of Infectious Diseases and Parasites. Seven (7) patients were diagnosed as asymptomatic carriers and the other 7 were diagnosed with chronic hepatitis. Among them, 2 were with moderate severity and 2 were mild. All patients were HBsAg (Hepatitis B surface antigen), HBeAg (Hepatitis B e antigen), and HBV DNA (Hepatitis B DNA quantification) positive. The 14 patients included 8 males and 6 females, all aged between 17–71 years.

III. Treatment:

Each patient received 3 ganoderma spores tablets (200 mg per tablet) per time and three times per day for 45 consecutive days ($1^{st}$ treatment course). The treatment was stopped for 15 days and then resumed for another 45 consecutive days ($2^{nd}$ treatment course).

IV. Observations:

1. Blood Samples were collected monthly. HBsAg, HBeAg and HBe-antibodies were tested using ELISA. The testing kit was provided by Chung-Shian Bioengineering Company.

2. Reagents for serum HBV DNA quantitation test (Digene Hybrid Capture II Assay) was provided by Chung-Shian Medical University.

3. Serum ALT activity was measured using a biochemical semiautomatic analytical instrument made in Italy.

V. Results:

A. Effects of Germination Activated Ganoderma Spores on HBeAg and HBV DNA

The results of ganoderma spores treatment on the 14 patients are shown in Table 21. In the beginning of the treatment, these 14 patients were all tested HBeAg and HBV DNA positive.

TABLE 21

Effects of Germination Activated Ganoderma Spores on HBeAg and HBV DNA

| | Treatment Duration | | | |
|---|---|---|---|---|
| | 1 month | 2 month | 3 month | 4 month |
| Negative HBeAg (HBeAg not detected) | 2 | 0 | 0 | 0 |
| Positive HBe Antibody | 1 | 2 | 1 | 1 |
| Negative HBV DNA | 0 | 3 | 1 | 1 |

As shown in Table 21, after the treatment of sporoderm-broken ganoderma spores for 1 month, 2 patients became HBeAg negative & 1 patient became HBeAb positive. After 2 months, 2 patients became HBeAb positive and 3 had negative HBV DNA. During the $3^{rd}$ and $4^{th}$ months of treatment, in each month, 1 patient became HBeAb positive and 1 had negative HBV DNA. The rest 2 patients initially had shown negative HBeAg but were reverted to HBeAg positive 2 months later. The 5 patients who had shown HBeAb positive also became HBV DNA negative. Among these 5 patients, one was HBeAg positive, HBV DNA negative. He later became HBeAg negative and HBeAb positive, but with an ALT level higher than before the treatment.

B. Effects of Germination Activated Ganoderma Spores on ASC (asymptomatic carriers) and CHB (chronic hepatitis B)

The therapeutic effects of ganoderma spores on ASC and CHB patients were similar and statistically insignificant.

C. Treatment Courses on Therapeutic Effects of Germination Activated Ganoderma Spores As shown in Table 22, the therapeutic effects after two courses of treatment with ganoderma spores are better than one course of treatment with ganoderma spores. As indicated above, the $1^{st}$ treatment course was continued for 45 days. After discontinued for 15 days later, the treatment was resumed ($2^{nd}$ treatment course) for additional 45 days.

TABLE 22

Treatment Courses on Therapeutic Effects of Ganoderma Spores

| | Case Number | Negative HBeAg | Positive HBeAb | Negative HBV DNA |
|---|---|---|---|---|
| $1^{st}$ treatment course | 7 | 1 | 1 | 1 |
| $2^{nd}$ treatment course | 7 | 1 | 4 | 4 |

D. Observations for Adverse Effects After Treatment with Germination Activated Ganoderma Spores All 14 patients completed the entire treatment program. Non has shown any fever or skin irritations. All patients maintained normal appetite and sleep pattern. The results of these studies indicate that the germination activated sporodern-broken ganoderma spores were clinically safe with no apparent adverse effects on patients.

Clinical Example 2

Clinical Observations

The following are individual observations on patents treated with sporoderm-broken ganoderma spores.

1. Patient N: male, age 36.
    Diagnosis: liver hepatitis B carrier; mother died of liver cancer "a few years ago".
    Patient N was given high dose of sporoderm-broken ganoderma spores between March, 1999 and September, 1999. In September, patient N's fatty liver and gall bladder polyps disappeared. Also, his HBV DNA was greatly reduced.

| Date | Observation | Change |
|---|---|---|
| March 1999 | Fatty liver Gall bladder polyps | |
| July 1999 | HBV DNA 3490 pg/ml | |
| September 1999 | HBV DNA 620 pg/ml Normal liver | Reduced to normal range |

2. Patient L: male, age 62.
    Patient L was diagnosed with hepatoma (tumor size: 5.1×6.6×7.7 cm) with tumor located at the portal vein region of the liver. He started high dose of ganoderma spores treatment in May, 1999. In August, 1999, X-ray data confirmed that his tumor reduced to 3.5×3.4×3 cm. Between May and August, 1999, ganoderma spores were the only medicine that patient L had taken.

| Date | Observation | Change |
|---|---|---|
| May 1999 | Confirmed liver cancer Tumor size 5.1 × 6.6 × 7.7 cm Other satellite tumors present | |
| August 1999 | Tumor size 3.5 × 3.4 × 3 cm | |

3. Patient C: Male, age 44.
    Patient C was diagnosed with hepatitis B and early liver cirrhosis, and was admitted to hospital since 1997. Patient

| Date | Observation | Change |
|---|---|---|
| March 1999 | Hepatitis B and jaundice Liver hepatitis B and only cirrhosis | Started treatment |
| Present | HBV DNA 5 pg/ml | |

4. Patient L-1: male, age 67
    Patient L-1 was diagnosed with poor glucose control for 10 years even after injection of insulin. In March, 1999, Patient L-1's hemoglobin Alc (HbAlc) was 16.4%. Patient L-1 started high dose of germination activated sporoderm-broken ganoderma spores treatment in March, 1999. In August, 1999, his HbAlc reduced to 10%, which was within the range of moderate glucose control.

| Date | Observation | Change |
|---|---|---|
| March 1999 | Hb Alc 16.4% | |
| August 1999 | Hb Alc 10% | |

Treatment started in March. Result: moderate glucose control.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modification.

What is claimed is:

1. A method for producing sporoderm-broken ganodenma spores comprising:
    soaking ganoderma spores in a solution which is selected from the group consisting of water, saline, and a nutritional solution to cause the spores to germinate;
    placing said germinated spores in a culture box to activate said germinated spores at relative humidity of 65–98% and temperature of 18–48° C. so as to enhance production of bioactive substances in said germination activated ganoderma spores; and
    treating the germination activated ganoderma spores with an enzyme with cell wall dissolving property to produce said sporoderm-broken ganodenna spores.

2. The method for producing sporoderm-broken ganoderma spores according to claim 1, wherein said enzyme is chitinase or cellulase.

3. The method according to claim 1, wherein wherein said spores are soaked in the solution for 30 minutes to 8 hours at no more than 50° C.

4. The method for producing germination activated ganoderma spores according to claim 3, wherein said spores are soaked in the solution for 2 to 4 hours.

5. The method according to claim 3, wherein said spores are soaked in the solution at 20 to 43° C.

6. The method according to claim 1, wherein said nutritional solution is at least one selected from the group consisting of coconut juice, malt extract, ganoderma sporocaip extract, ganoderma capillitia extract, culture solution containing biotin, and culture solution containing monobasic potassium phosphate and magnesium sulfate.

7. The method according to claim 1, wherein said solution is 0.1–5 times the weight of said spores.

8. The method according to claim 1, wherein said bioactive substances are selected from the group consisting of active genes and promoters, active enxymes, sterols, cytokines, interferons, lactone A, ganoderma acid A, triterpenes, polysaccharides, vitamins, superoxide dismutases (SOD), vitamin E, glycoproteins, and growth factors.

9. A method for extracting bioactive substances from germination activated ganoderma spores comprising:
   drying the sporoderm-broken ganoderma spores according to claim 1 at low temperature; and
   extracting the dried sporoderm-broken ganoderma spores.

10. The method for extracting bioactive substances from germination activated ganoderma spores according to claim 9, wherein said drying is freeze-drying or vacuum-drying.

11. The method for extracting bioactive substances from germination activated ganoderma spores according to claim 9, wherein said bioactive substances are extracted by water, alcohol, or thin film condensation.

12. A method for producing sporoderm-broken ganoderma spores comprising:
   soaking ganoderma spores in a solution which is selected from the group consisting of water, saline, and a nutritional solution to cause the spores to germinate;
   placing said germinated spores in a culture box to activate said germinated spores at relative humidity of 65–98% and temperature of 18–48° C. to enhance production of bioactive substances in said germination activated spores; and
   treating the germination activated ganodenna spores with a mechanical force to produce said sporoderm-broken ganoderma spores.

13. The method for producing sporoderm-broken ganoderma spores according to claim 12, wherein said mechanical force is at least one selected from the group consisting of micronization, roll pressing, grinding, ultrasound, and super high pressure microstream treatment.

14. The method according to claim 12, wherein wherein said spores are soaked in the solution for 30 minutes to 8 hours at no more than 50° C.

15. The method for producing germination activated ganoderma spores according to claim 14, wherein said spores are soaked in the solution for 2 to 4 hours.

16. The method according to claim 14, wherein said spores are soaked in the solution at 20 to 43° C.

17. The method according to claim 12, wherein said nutritional solution is at least one selected from the group consisting of coconut juice, malt extract, ganoderma sporocarp extract, ganoderma capillitia extract, culture solution containing biotin, and culture solution containing monobasic potassium phosphate and magnesium sulfate.

18. The method according to claim 12, wherein said solution is 0.1–5 times the weight of said spores.

19. The method according to claim 12, wherein said bioactive substances are selected from the group consisting of active genes and promoters, active enxymes, sterols, cytokines, interferons, lactone A, ganoderma acid A, triterpenes, polysaccharides, vitamins, superoxide dismutases (SOD), vitamin E, glycoproteins, and growth factors.

20. A method for extracting bioactive substances from germination activated ganoderma spores comprising:
   drying the sporoderm-broken ganoderma spores according to claim 12 at low temperature; and
   extracting the dried sporoderm-broken ganodenna spores.

21. The method for extracting bioactive substances from germination activated ganoderma spores according to calim 20, wherein said drying is freeze-drying or vacuum-drying.

22. The method for extracting bioactive substances from germination activated ganoderma spores according to claim 20, wherein said bioactive substances are extracted by water, alcohol, or thin film condensation.

\* \* \* \* \*

UNITED STATES PATENT AND TRADEMARK OFFICE
CERTIFICATE OF CORRECTION

PATENT NO.    : 6,316,002 B1
DATED         : November 13, 2001
INVENTOR(S)   : Xin Liu and Chee-Keung Chung Page 1 of 1

It is certified that error appears in the above-identified patent and that said Letters Patent is hereby corrected as shown below:

Title page, Item [54] and Column 1, line 1,
Delete the word "RED" should read -- GERMINATION ACTIVATED GANODERMA LUCIDUM SPORES AND METHOD FOR PRODUCING THE SAME --
ABSTRACT, line 2, delete the word "RED"

Column 2,
Line 65, delete the word "RED"

Column 4,
Lines 8, 27, 32, 43, 48, 59 and 61, delete the word "RED"

Column 6,
Lines 5, 17, 21, 31, 42, 53 and 63, delete the word "RED"

Column 7,
Lines 14, 25, 54 and 67, delete the word "RED"

Column 8,
Lines 16, 29, 34, 46, 56 and 61, delete the word "RED"

Signed and Sealed this

Ninth Day of April, 2002

*Attest:*

*Attesting Officer*

JAMES E. ROGAN
*Director of the United States Patent and Trademark Office*